United States Patent
Adie et al.

(10) Patent No.: US 10,159,604 B2
(45) Date of Patent: *Dec. 25, 2018

(54) WOUND DRESSING AND METHOD OF USE

(71) Applicant: Smith & Nephew PLC, London (GB)

(72) Inventors: Gordon Campbell Adie, Cottingham (GB); Sarah Jenny Collinson, Hull (GB); Christopher John Fryer, York (GB); Edward Yerbury Hartwell, Hull (GB); Derek Nicolini, Hull (GB); Yannick Louis Peron, East Yorkshire (GB)

(73) Assignee: Smith & Nephew PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/633,670

(22) Filed: Jun. 26, 2017

(65) Prior Publication Data
US 2017/0290709 A1    Oct. 12, 2017

Related U.S. Application Data

(63) Continuation of application No. 14/715,399, filed on May 18, 2015, which is a continuation of application
(Continued)

(30) Foreign Application Priority Data

Apr. 27, 2010 (GB) .................... 1006983.9
Apr. 27, 2010 (GB) .................... 1006985.4
(Continued)

(51) Int. Cl.
*A61M 35/00* (2006.01)
*A61M 1/00* (2006.01)
(Continued)

(52) U.S. Cl.
CPC ...... *A61F 13/00068* (2013.01); *A61F 13/022* (2013.01); *A61F 13/0206* (2013.01);
(Continued)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS 2,280,915 A    4/1942 Johnson
2,568,933 A    9/1951 Robbins
(Continued)

FOREIGN PATENT DOCUMENTS

AU    2015201022    9/2016
CA    2 705 898    5/2009
(Continued)

OTHER PUBLICATIONS

Achterberg, V., Ph.D., Hydroactive dressings and serum proteins: an in vitro study, Journal of Wound Care, February, vol. 5, No. 2, 1996, pp. 79-82.
(Continued)

*Primary Examiner* — Tatyana Zalukaeva
*Assistant Examiner* — Ilya Treyger
(74) *Attorney, Agent, or Firm* — Knobbe, Martens, Olson & Bear, LLP

(57) ABSTRACT

A system, method, and apparatus are disclosed for dressing a wound. The apparatus comprises a liquid and gas permeable transmission layer, an absorbent layer for absorbing wound exudate, the absorbent layer overlying the transmission layer, a gas impermeable cover layer overlying the absorbent layer and comprising a first orifice, wherein the cover layer is moisture vapor permeable.

30 Claims, 21 Drawing Sheets

Related U.S. Application Data

No. 13/092,042, filed on Apr. 21, 2011, now Pat. No. 9,061,095.

(30) Foreign Application Priority Data

| Apr. 27, 2010 | (GB) | ................................ 1006986.2 |
| Apr. 27, 2010 | (GB) | ................................ 1006988.8 |
| May 19, 2010 | (GB) | ................................ 1008347.5 |

(51) Int. Cl.
  *A61F 13/00* (2006.01)
  *A61F 13/02* (2006.01)
  *A61M 27/00* (2006.01)

(52) U.S. Cl.
  CPC ......... *A61F 13/0209* (2013.01); *A61M 1/008* (2013.01); *A61M 1/009* (2014.02); *A61M 1/0088* (2013.01); *A61F 13/00012* (2013.01); *A61F 2013/0054* (2013.01); *A61F 2013/00174* (2013.01); *A61F 2013/00238* (2013.01); *A61F 2013/00536* (2013.01); *A61M 2202/0014* (2013.01); *A61M 2205/7536* (2013.01)

(56) References Cited

U.S. PATENT DOCUMENTS

| 2,632,443 | A |   | 3/1953  | Lesher |
| 2,682,873 | A |   | 7/1954  | Evans et al. |
| 2,877,765 | A |   | 3/1959  | Bunyan |
| 2,889,039 | A |   | 6/1959  | Schladermundt et al. |
| 3,073,304 | A |   | 1/1963  | Schaar |
| 3,115,138 | A |   | 12/1963 | McElvenny et al. |
| 3,367,332 | A |   | 2/1968  | Groves |
| 3,572,340 | A |   | 3/1971  | Lloyd et al. |
| 3,874,387 | A |   | 4/1975  | Barbieri |
| 3,972,328 | A |   | 8/1976  | Chen |
| 3,993,080 | A |   | 11/1976 | Loseff |
| 4,029,598 | A |   | 6/1977  | Neisius et al. |
| 4,112,947 | A |   | 9/1978  | Nehring |
| 4,117,551 | A |   | 9/1978  | Books et al. |
| 4,136,696 | A |   | 1/1979  | Nehring |
| 4,184,510 | A |   | 1/1980  | Murry et al. |
| 4,217,894 | A |   | 8/1980  | Franetzki |
| 4,219,019 | A |   | 8/1980  | Coates |
| 4,224,945 | A |   | 9/1980  | Cohen |
| 4,294,240 | A |   | 10/1981 | Thill |
| 4,316,466 | A |   | 2/1982  | Babb |
| 4,382,441 | A |   | 5/1983  | Svedman |
| 4,465,485 | A |   | 8/1984  | Kashmer et al. |
| 4,534,356 | A |   | 8/1985  | Papadakis |
| 4,538,920 | A |   | 9/1985  | Drake et al. |
| 4,541,426 | A |   | 9/1985  | Webster |
| 4,573,965 | A |   | 3/1986  | Russo |
| 4,655,754 | A |   | 4/1987  | Richmond et al. |
| 4,655,766 | A |   | 4/1987  | Theeuwes et al. |
| 4,710,165 | A |   | 12/1987 | McNeil et al. |
| 4,728,499 | A |   | 3/1988  | Fehder |
| 4,753,536 | A |   | 6/1988  | Spehar et al. |
| 4,767,026 | A |   | 8/1988  | Keller |
| 4,771,919 | A |   | 9/1988  | Ernst |
| 4,778,446 | A |   | 10/1988 | Jensen |
| 4,792,328 | A |   | 12/1988 | Beck et al. |
| 4,813,942 | A |   | 3/1989  | Alvarez |
| 4,826,494 | A |   | 5/1989  | Richmond et al. |
| 4,828,546 | A |   | 5/1989  | McNeil et al. |
| 4,846,164 | A |   | 7/1989  | Martz |
| 4,872,450 | A |   | 10/1989 | Austad |
| 4,921,488 | A |   | 5/1990  | Maitz et al. |
| 4,929,477 | A |   | 5/1990  | Will |
| 4,936,834 | A |   | 6/1990  | Beck et al. |
| 4,969,880 | A |   | 11/1990 | Zamierowski |
| 4,972,829 | A |   | 11/1990 | Knerr |
| 4,994,022 | A |   | 2/1991  | Steffler et al. |
| 5,010,115 | A |   | 4/1991  | Grisoni |
| 5,010,883 | A |   | 4/1991  | Rawlings et al. |
| 5,055,198 | A |   | 10/1991 | Shettigar |
| 5,056,510 | A |   | 10/1991 | Gilman |
| 5,064,653 | A |   | 11/1991 | Sessions et al. |
| 5,073,172 | A |   | 12/1991 | Fell |
| 5,080,493 | A |   | 1/1992  | McKown et al. |
| 5,100,396 | A |   | 3/1992  | Zamierowski |
| 5,115,801 | A |   | 5/1992  | Cartmell et al. |
| 5,134,994 | A |   | 8/1992  | Say |
| 5,145,906 | A | * | 9/1992  | Chambers ................. C08F 8/00 524/732 |
| 5,152,757 | A |   | 10/1992 | Eriksson |
| 5,160,328 | A |   | 11/1992 | Cartmell et al. |
| 5,167,613 | A |   | 12/1992 | Karami et al. |
| 5,176,663 | A |   | 1/1993  | Svedman et al. |
| 5,181,905 | A |   | 1/1993  | Flam |
| 5,197,945 | A |   | 3/1993  | Cole et al. |
| 5,215,519 | A |   | 6/1993  | Shettigar |
| 5,234,419 | A |   | 8/1993  | Bryant et al. |
| 5,238,732 | A |   | 8/1993  | Krishnan |
| 5,249,709 | A |   | 10/1993 | Duckworth et al. |
| 5,261,893 | A |   | 11/1993 | Zamierowski |
| 5,266,326 | A |   | 11/1993 | Barry et al. |
| 5,266,928 | A |   | 11/1993 | Johnson |
| 5,267,952 | A |   | 12/1993 | Gardner |
| 5,279,608 | A |   | 1/1994  | Cherif Cheikh |
| 5,328,614 | A |   | 7/1994  | Matsumura |
| 5,333,760 | A |   | 8/1994  | Simmen et al. |
| 5,336,219 | A |   | 8/1994  | Krantz |
| 5,354,261 | A |   | 10/1994 | Clark et al. |
| 5,358,494 | A |   | 10/1994 | Svedman |
| 5,364,381 | A |   | 11/1994 | Soga et al. |
| 5,380,280 | A |   | 1/1995  | Peterson |
| 5,380,294 | A |   | 1/1995  | Persson |
| 5,397,316 | A |   | 3/1995  | LaVon et al. |
| 5,437,651 | A |   | 8/1995  | Todd et al. |
| 5,445,604 | A |   | 8/1995  | Lang |
| 5,447,492 | A |   | 9/1995  | Cartmell et al. |
| 5,456,660 | A |   | 10/1995 | Reich et al. |
| 5,456,745 | A |   | 10/1995 | Rorefer et al. |
| 5,480,377 | A |   | 1/1996  | Cartmell et al. |
| 5,489,280 | A |   | 2/1996  | Russell |
| 5,497,788 | A |   | 3/1996  | Inman et al. |
| 5,498,338 | A |   | 3/1996  | Kruger et al. |
| 5,527,293 | A |   | 6/1996  | Zamierowski |
| 5,538,500 | A |   | 7/1996  | Peterson |
| 5,549,584 | A |   | 8/1996  | Gross |
| 5,562,107 | A |   | 10/1996 | Lavender et al. |
| 5,579,765 | A |   | 12/1996 | Cox et al. |
| 5,582,596 | A |   | 12/1996 | Fukunaga et al. |
| 5,583,114 | A |   | 12/1996 | Barrows et al. |
| 5,603,946 | A |   | 2/1997  | Constantine |
| 5,609,271 | A |   | 3/1997  | Keller et al. |
| 5,612,050 | A |   | 3/1997  | Rowe et al. |
| 5,624,423 | A |   | 4/1997  | Anjur et al. |
| 5,636,643 | A |   | 6/1997  | Argenta et al. |
| 5,637,080 | A |   | 6/1997  | Geng |
| 5,643,189 | A |   | 7/1997  | Masini |
| 5,645,081 | A |   | 7/1997  | Argenta et al. |
| 5,660,823 | A |   | 8/1997  | Chakrabarti et al. |
| 5,662,599 | A |   | 9/1997  | Reich et al. |
| 5,702,356 | A |   | 12/1997 | Hathman |
| 5,704,905 | A |   | 1/1998  | Jensen et al. |
| 5,707,499 | A |   | 1/1998  | Joshi et al. |
| 5,713,384 | A |   | 2/1998  | Roach et al. |
| 5,717,030 | A |   | 2/1998  | Dunn et al. |
| 5,747,064 | A |   | 5/1998  | Burnett et al. |
| 5,759,570 | A |   | 6/1998  | Arnold |
| 5,776,193 | A |   | 7/1998  | Kwan et al. |
| 5,785,688 | A |   | 7/1998  | Joshi et al. |
| 5,804,021 | A |   | 9/1998  | Abuto et al. |
| 5,827,213 | A |   | 10/1998 | Jensen |
| 5,833,646 | A |   | 11/1998 | Masini |
| 5,834,007 | A |   | 11/1998 | Kubota |
| 5,840,052 | A |   | 11/1998 | Johns |
| 5,843,011 | A |   | 12/1998 | Lucas |
| 5,843,025 | A |   | 12/1998 | Shaari |
| 5,852,126 | A |   | 12/1998 | Barnard et al. |

(56) References Cited

U.S. PATENT DOCUMENTS

| | | |
|---|---|---|
| 5,868,724 A | 2/1999 | Dierckes, Jr. et al. |
| 5,868,933 A | 2/1999 | Patrick et al. |
| 5,874,500 A | 2/1999 | Rhee et al. |
| 5,876,611 A | 3/1999 | Shettigar |
| 5,897,541 A | 4/1999 | Uitenbrock et al. |
| 5,945,115 A | 8/1999 | Dunn et al. |
| 5,962,010 A | 10/1999 | Greff et al. |
| 5,964,723 A | 10/1999 | Augustine |
| 5,981,822 A | 11/1999 | Addison |
| 5,998,472 A | 12/1999 | Berger et al. |
| 6,040,493 A | 3/2000 | Cooke et al. |
| 6,071,267 A | 6/2000 | Zamierowski |
| 6,075,177 A | 6/2000 | Bahia et al. |
| 6,103,951 A | 8/2000 | Freeman |
| 6,124,520 A | 9/2000 | Roberts |
| 6,124,521 A | 9/2000 | Roberts |
| 6,135,116 A | 10/2000 | Vogel et al. |
| 6,142,982 A | 11/2000 | Hunt et al. |
| 6,143,352 A | 11/2000 | Clark et al. |
| 6,165,201 A | 12/2000 | Sawhney et al. |
| 6,167,613 B1 | 1/2001 | Karami |
| 6,168,788 B1 | 1/2001 | Wortham |
| 6,168,800 B1 | 1/2001 | Dobos et al. |
| 6,203,654 B1 | 3/2001 | McFall et al. |
| 6,207,875 B1 | 3/2001 | Lindqvist et al. |
| 6,214,332 B1 | 4/2001 | Askill et al. |
| 6,225,523 B1 | 5/2001 | Masini |
| 6,252,129 B1 | 6/2001 | Coffee |
| 6,254,567 B1 | 7/2001 | Treu et al. |
| 6,255,552 B1 | 7/2001 | Cummings et al. |
| 6,287,521 B1 | 9/2001 | Quay et al. |
| 6,291,050 B1 | 9/2001 | Cree et al. |
| 6,297,422 B1 | 10/2001 | Hansen et al. |
| 6,297,423 B1 | 10/2001 | Schoenfeldt et al. |
| 6,345,623 B1 | 2/2002 | Heaton et al. |
| 6,362,390 B1 | 3/2002 | Carlucci et al. |
| 6,391,294 B1 | 5/2002 | Dettmar et al. |
| 6,398,761 B1 | 6/2002 | Bills et al. |
| 6,398,767 B1 | 6/2002 | Fleischmann |
| 6,440,167 B2 | 8/2002 | Shimizu |
| 6,447,802 B2 | 9/2002 | Sessions et al. |
| 6,450,773 B1 | 9/2002 | Upton |
| 6,458,109 B1 | 10/2002 | Henley et al. |
| 6,465,708 B1 | 10/2002 | Augustine |
| 6,468,295 B2 | 10/2002 | Augustine et al. |
| 6,471,982 B1 | 10/2002 | Lydon et al. |
| 6,486,285 B2 | 11/2002 | Fujita |
| 6,491,684 B1 | 12/2002 | Joshi et al. |
| 6,495,127 B1 | 12/2002 | Wallace et al. |
| 6,506,175 B1 | 1/2003 | Goldstein |
| 6,509,031 B1 | 1/2003 | Miller et al. |
| 6,521,251 B2 | 2/2003 | Askill et al. |
| 6,528,696 B1 | 3/2003 | Ireland |
| 6,547,467 B2 | 4/2003 | Quintero |
| 6,553,998 B2 | 4/2003 | Heaton et al. |
| 6,566,575 B1 | 5/2003 | Stickels et al. |
| 6,575,940 B1 | 6/2003 | Levinson et al. |
| 6,586,653 B2 | 7/2003 | Graeme, III et al. |
| 6,596,704 B1 | 7/2003 | Court et al. |
| 6,599,262 B1 | 7/2003 | Masini |
| 6,613,953 B1 | 9/2003 | Altura |
| 6,626,891 B2 | 9/2003 | Ohmstede |
| 6,627,216 B2 | 9/2003 | Brandt et al. |
| 6,629,774 B1 | 10/2003 | Guruendeman |
| 6,648,862 B2 | 11/2003 | Watson |
| 6,673,028 B1 | 1/2004 | Argenta et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,706,940 B2 | 3/2004 | Worthley |
| 6,719,742 B1 | 4/2004 | McCormack et al. |
| 6,730,299 B1 | 5/2004 | Tayot et al. |
| 6,752,794 B2 | 6/2004 | Lockwood et al. |
| 6,755,807 B2 | 6/2004 | Risk et al. |
| 6,762,337 B2 | 7/2004 | Boukanov et al. |
| 6,764,459 B1 | 7/2004 | Donaldson |
| 6,764,462 B2 | 7/2004 | Risk, Jr. et al. |
| 6,767,334 B1 | 7/2004 | Randolph |
| 6,775,807 B2 | 8/2004 | Lowther et al. |
| 6,776,769 B2 | 8/2004 | Smith |
| 6,787,682 B2 | 9/2004 | Gilman |
| 6,790,438 B1 | 9/2004 | Constancis et al. |
| 6,814,079 B2 | 11/2004 | Heaton et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,856,821 B2 | 2/2005 | Johnson |
| 6,936,037 B2 | 8/2005 | Bubb et al. |
| 6,951,553 B2 | 10/2005 | Bubb et al. |
| 6,960,179 B2 | 11/2005 | Gura |
| 6,977,323 B1 | 12/2005 | Swenson |
| 6,979,324 B2 | 12/2005 | Bybordi et al. |
| 6,994,702 B1 | 2/2006 | Johnson |
| 6,998,511 B2 | 2/2006 | Worthley |
| 7,004,915 B2 | 2/2006 | Boynton et al. |
| 7,022,113 B2 | 4/2006 | Lockwood et al. |
| 7,049,478 B1 | 5/2006 | Smith et al. |
| 7,067,709 B2 | 6/2006 | Murata et al. |
| 7,070,584 B2 | 7/2006 | Johnson et al. |
| 7,077,832 B2 | 7/2006 | Fleischmann |
| 7,108,683 B2 | 9/2006 | Zamierowski |
| 7,117,869 B2 | 10/2006 | Heaton et al. |
| 7,118,545 B2 | 10/2006 | Boyde |
| 7,128,735 B2 | 10/2006 | Weston |
| 7,129,210 B2 | 10/2006 | Lowinger et al. |
| 7,195,624 B2 | 3/2007 | Lockwood |
| 7,214,202 B1 | 5/2007 | Vogel et al. |
| 7,216,651 B2 | 5/2007 | Argenta et al. |
| 7,238,850 B2 | 7/2007 | Shimanuki |
| 7,294,751 B2 | 11/2007 | Propp et al. |
| 7,294,752 B1 | 11/2007 | Propp |
| 7,303,757 B2 | 12/2007 | Schankereli et al. |
| 7,335,809 B2 | 2/2008 | Riesinger |
| 7,338,482 B2 | 3/2008 | Lockwood et al. |
| 7,361,184 B2 | 4/2008 | Joshi |
| 7,381,211 B2 | 6/2008 | Zamierowski |
| 7,381,859 B2 | 6/2008 | Hunt et al. |
| 7,429,689 B2 | 9/2008 | Chen et al. |
| 7,438,705 B2 | 10/2008 | Karpowicz et al. |
| 7,468,471 B2 | 12/2008 | Sigurjonsson et al. |
| 7,470,830 B2 | 12/2008 | Sigurjonsson et al. |
| 7,476,205 B2 | 1/2009 | Erdmann |
| 7,485,112 B2 | 2/2009 | Karpowicz et al. |
| 7,494,482 B2 | 2/2009 | Orgill et al. |
| 7,503,910 B2 | 3/2009 | Adahan |
| 7,507,870 B2 | 3/2009 | Nielsen et al. |
| 7,511,187 B2 | 3/2009 | Kelly |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood |
| 7,563,940 B2 | 7/2009 | Kurata |
| 7,569,742 B2 | 8/2009 | Haggstrom et al. |
| 7,576,256 B2 | 8/2009 | Björnberg et al. |
| 7,601,129 B2 | 10/2009 | Aali |
| 7,605,298 B2 | 10/2009 | Bechert et al. |
| 7,612,247 B2 | 11/2009 | Oyaski |
| 7,615,036 B2 | 11/2009 | Joshi et al. |
| 7,622,629 B2 | 11/2009 | Aail |
| 7,625,362 B2 | 12/2009 | Boehringer et al. |
| 7,645,269 B2 | 1/2010 | Zamierowski |
| 7,676,400 B1 | 3/2010 | Dillon |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,722,582 B2 | 5/2010 | Lina et al. |
| 7,723,560 B2 | 5/2010 | Lockwood et al. |
| 7,723,561 B2 | 5/2010 | Propp |
| 7,731,702 B2 | 6/2010 | Bybordi et al. |
| 7,745,681 B1 | 6/2010 | Ferguson |
| 7,749,531 B2 | 7/2010 | Booher |
| 7,753,894 B2 | 7/2010 | Blott et al. |

(56) References Cited

U.S. PATENT DOCUMENTS

| | | |
|---|---|---|
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,794,438 B2 | 9/2010 | Henley et al. |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,815,616 B2 | 10/2010 | Boehringer et al. |
| 7,816,577 B2 | 10/2010 | Aali |
| 7,828,782 B2 | 11/2010 | Suzuki |
| 7,838,716 B2 | 11/2010 | de Luis et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,858,838 B2 | 12/2010 | Holm et al. |
| 7,862,831 B2 | 1/2011 | Wang et al. |
| 7,880,050 B2 | 2/2011 | Robinson et al. |
| 7,884,258 B2 | 2/2011 | Boehringer et al. |
| 7,896,823 B2 | 3/2011 | Mangrum et al. |
| 7,896,856 B2 | 3/2011 | Petrosenko et al. |
| 7,909,805 B2 | 3/2011 | Weston |
| 7,910,135 B2 | 3/2011 | St. John et al. |
| 7,910,791 B2 | 3/2011 | Coffey |
| 7,922,703 B2 | 4/2011 | Riesinger |
| 7,927,318 B2 | 4/2011 | Risk, Jr. et al. |
| 7,931,630 B2 | 4/2011 | Nishtala et al. |
| 7,935,066 B2 | 5/2011 | Shives et al. |
| 7,959,624 B2 | 6/2011 | Riesinger |
| 7,964,766 B2 | 6/2011 | Blott et al. |
| 7,976,519 B2 | 7/2011 | Bubb et al. |
| 7,982,087 B2 | 7/2011 | Greener et al. |
| D642,594 S | 8/2011 | Mattson et al. |
| 7,988,673 B2 | 8/2011 | Wright et al. |
| 7,998,125 B2 | 8/2011 | Weston |
| 8,007,164 B2 | 8/2011 | Miyano et al. |
| 8,007,257 B2 | 8/2011 | Heaton et al. |
| 8,021,347 B2 | 9/2011 | Vitaris et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,331 B2 | 11/2011 | Zamierowski |
| 8,080,702 B2 | 12/2011 | Blott et al. |
| 8,084,663 B2 | 12/2011 | Watson, Jr. |
| 8,092,436 B2 | 1/2012 | Christensen |
| 8,097,272 B2 | 1/2012 | Addison |
| 8,100,887 B2 | 1/2012 | Weston et al. |
| 8,105,295 B2 | 1/2012 | Blott et al. |
| 8,118,794 B2 | 2/2012 | Weston et al. |
| 8,119,160 B2 | 2/2012 | Looney et al. |
| 8,133,211 B2 | 3/2012 | Cavanaugh, II et al. |
| 8,147,468 B2 | 4/2012 | Barta et al. |
| 8,152,785 B2 | 4/2012 | Vitaris |
| 8,158,844 B2 | 4/2012 | McNeil |
| 8,162,907 B2 | 4/2012 | Heagle |
| 8,162,909 B2 | 4/2012 | Blott et al. |
| 8,168,848 B2 | 5/2012 | Lockwood et al. |
| 8,188,331 B2 | 5/2012 | Barta et al. |
| 8,202,261 B2 | 6/2012 | Kazala, Jr. et al. |
| 8,207,392 B2 | 6/2012 | Haggstrom et al. |
| 8,211,071 B2 | 7/2012 | Mormino et al. |
| 8,212,101 B2 | 7/2012 | Propp |
| 8,215,929 B2 | 7/2012 | Shen et al. |
| 8,226,942 B2 | 7/2012 | Charier et al. |
| 8,235,955 B2 | 8/2012 | Blott et al. |
| 8,235,972 B2 | 8/2012 | Adahan |
| 8,241,261 B2 | 8/2012 | Randolph et al. |
| 8,246,607 B2 | 8/2012 | Karpowicz et al. |
| 8,251,979 B2 | 8/2012 | Malhi |
| 8,252,971 B2 | 8/2012 | Aali et al. |
| 8,257,327 B2 | 9/2012 | Blott et al. |
| 8,257,328 B2 | 9/2012 | Augustine et al. |
| 8,267,908 B2 | 9/2012 | Coulthard |
| 8,273,368 B2 | 9/2012 | Ambrosio et al. |
| 8,282,611 B2 | 10/2012 | Weston |
| 8,294,586 B2 | 10/2012 | Pidgeon et al. |
| 8,303,552 B2 | 11/2012 | Weston |
| 8,308,714 B2 | 11/2012 | Weston et al. |
| 8,314,283 B2 | 11/2012 | Kingsford et al. |
| 8,317,774 B2 | 11/2012 | Adahan |
| 8,323,264 B2 | 12/2012 | Weston et al. |
| 8,328,858 B2 | 12/2012 | Barsky et al. |
| 8,348,910 B2 | 1/2013 | Blott et al. |
| 8,372,049 B2 | 2/2013 | Jaeb et al. |
| 8,372,050 B2 | 2/2013 | Jaeb et al. |
| 8,376,972 B2 | 2/2013 | Fleischmann |
| 8,403,899 B2 | 3/2013 | Sherman |
| 8,404,921 B2 | 3/2013 | Lee et al. |
| D679,819 S | 4/2013 | Peron |
| D679,820 S | 4/2013 | Peron |
| 8,409,159 B2 | 4/2013 | Hu et al. |
| 8,410,189 B2 | 4/2013 | Carnahan et al. |
| 8,425,478 B2 | 4/2013 | Olson |
| 8,444,612 B2 | 5/2013 | Patel et al. |
| 8,449,509 B2 | 5/2013 | Weston |
| 8,460,255 B2 | 6/2013 | Joshi et al. |
| 8,494,349 B2 | 7/2013 | Gordon |
| 8,506,554 B2 | 8/2013 | Adahan |
| 8,535,283 B2 | 9/2013 | Heaton et al. |
| 8,535,296 B2 | 9/2013 | Blott et al. |
| 8,540,687 B2 | 9/2013 | Henley et al. |
| 8,545,466 B2 | 10/2013 | Andresen et al. |
| 8,556,871 B2 | 10/2013 | Mormino et al. |
| 8,568,386 B2 | 10/2013 | Malhi |
| 8,569,566 B2 | 10/2013 | Blott et al. |
| 8,624,077 B2 | 1/2014 | Rosenberg |
| 8,628,505 B2 | 1/2014 | Weston |
| 8,641,691 B2 | 2/2014 | Fink |
| 8,663,198 B2 | 3/2014 | Buan et al. |
| 8,679,079 B2 | 3/2014 | Heaton et al. |
| 8,680,360 B2 | 3/2014 | Greener et al. |
| 8,715,256 B2 | 5/2014 | Greener |
| 8,734,410 B2 | 5/2014 | Hall et al. |
| 8,753,670 B2 | 6/2014 | Delmotte |
| 8,764,732 B2 | 7/2014 | Hartwell |
| 8,784,392 B2 | 7/2014 | Vess et al. |
| 8,791,316 B2 | 7/2014 | Greener |
| 8,795,243 B2 | 8/2014 | Weston |
| 8,795,244 B2 | 8/2014 | Randolph et al. |
| 8,795,247 B2 | 8/2014 | Bennett et al. |
| 8,795,635 B2 | 8/2014 | Tamarkin et al. |
| 8,795,713 B2 | 8/2014 | Makower et al. |
| 8,795,800 B2 | 8/2014 | Evans |
| 8,801,685 B2 | 8/2014 | Armstrong et al. |
| 8,808,274 B2 | 8/2014 | Hartwell |
| 8,814,842 B2 | 8/2014 | Coulthard et al. |
| 8,829,263 B2 | 9/2014 | Haggstrom et al. |
| 8,834,451 B2 | 9/2014 | Blott et al. |
| 8,834,452 B2 | 9/2014 | Hudspeth et al. |
| 8,843,327 B2 | 9/2014 | Vernon-Harcourt et al. |
| 8,864,748 B2 | 10/2014 | Coulthard et al. |
| 8,915,895 B2 | 12/2014 | Jaeb et al. |
| 8,916,742 B2 | 12/2014 | Smith |
| 8,956,336 B2 | 2/2015 | Haggstrom et al. |
| 8,968,773 B2 | 3/2015 | Thomas et al. |
| 9,012,714 B2 | 4/2015 | Fleischmann |
| 9,028,872 B2 | 5/2015 | Gaserod et al. |
| 9,033,942 B2 | 5/2015 | Vess |
| 9,044,579 B2 | 6/2015 | Blott et al. |
| 9,061,095 B2 | 6/2015 | Adie et al. |
| 9,168,330 B2 | 10/2015 | Joshi et al. |
| 9,180,231 B2 | 11/2015 | Greener |
| 9,198,801 B2 | 12/2015 | Weston |
| 9,199,012 B2 | 12/2015 | Vitaris et al. |
| 9,220,822 B2 | 12/2015 | Hartwell et al. |
| 9,302,033 B2 | 4/2016 | Riesinger |
| 9,375,353 B2 | 6/2016 | Vitaris et al. |
| 9,375,521 B2 | 6/2016 | Hudspeth et al. |
| 9,381,283 B2 | 7/2016 | Adams et al. |
| 9,421,309 B2 | 8/2016 | Robinson et al. |
| 9,446,178 B2 | 9/2016 | Blott et al. |

(56) References Cited

U.S. PATENT DOCUMENTS

| | | |
|---|---|---|
| 9,452,248 B2 | 9/2016 | Blott et al. |
| 9,629,986 B2 | 4/2017 | Patel et al. |
| 9,820,888 B2 | 11/2017 | Greener et al. |
| 2001/0004082 A1 | 6/2001 | Keller et al. |
| 2001/0034499 A1 | 10/2001 | Sessions et al. |
| 2001/0043913 A1 | 11/2001 | Spaans et al. |
| 2001/0043943 A1 | 11/2001 | Coffey |
| 2001/0051178 A1 | 12/2001 | Blatchford et al. |
| 2002/0002209 A1 | 1/2002 | Mork |
| 2002/0019602 A1 | 2/2002 | Geng |
| 2002/0038826 A1 | 4/2002 | Hurray et al. |
| 2002/0052570 A1 | 5/2002 | Naimer |
| 2002/0110672 A1 | 8/2002 | Muratore-Pallatino et al. |
| 2002/0122771 A1 | 9/2002 | Holland et al. |
| 2002/0143286 A1 | 10/2002 | Tumey |
| 2002/0145007 A1 | 10/2002 | Sawhney et al. |
| 2002/0169405 A1 | 11/2002 | Roberts |
| 2002/0183702 A1 | 12/2002 | Henley et al. |
| 2002/0187182 A1 | 12/2002 | Kramer et al. |
| 2002/0198490 A1 | 12/2002 | Wirt et al. |
| 2003/0009122 A1 | 1/2003 | Veras |
| 2003/0021775 A1 | 1/2003 | Freeman |
| 2003/0040478 A1 | 2/2003 | Drucker et al. |
| 2003/0045825 A1 | 3/2003 | Etheredge, III |
| 2003/0050590 A1 | 3/2003 | Kirsch |
| 2003/0069535 A1 | 4/2003 | Shalaby |
| 2003/0069563 A1 | 4/2003 | Johnson |
| 2003/0114818 A1 | 6/2003 | Benecke et al. |
| 2003/0125649 A1 | 7/2003 | Mcintosh et al. |
| 2003/0143189 A1 | 7/2003 | Askill et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0180341 A1 | 9/2003 | Gooch et al. |
| 2003/0183653 A1 | 10/2003 | Bills |
| 2003/0199800 A1 | 10/2003 | Levin |
| 2003/0203011 A1 | 10/2003 | Abuelyaman et al. |
| 2003/0212357 A1 | 11/2003 | Pace |
| 2003/0212359 A1 | 11/2003 | Butler |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2004/0019337 A1 | 1/2004 | Moberg-Alehammar et al. |
| 2004/0019342 A1 | 1/2004 | Nagasuna et al. |
| 2004/0033466 A1 | 2/2004 | Shellard et al. |
| 2004/0037897 A1 | 2/2004 | Benjamin et al. |
| 2004/0039391 A1 | 2/2004 | Argenta et al. |
| 2004/0049187 A1 | 3/2004 | Burnett et al. |
| 2004/0054338 A1 | 3/2004 | Bybordi et al. |
| 2004/0057855 A1 | 3/2004 | Gerlach et al. |
| 2004/0064111 A1 | 4/2004 | Lockwood et al. |
| 2004/0073152 A1 | 4/2004 | Karason et al. |
| 2004/0078011 A1 | 4/2004 | Stevens |
| 2004/0106888 A1 | 6/2004 | Lutri et al. |
| 2004/0122434 A1 | 6/2004 | Argenta et al. |
| 2004/0127863 A1 | 7/2004 | Bubb et al. |
| 2004/0138602 A1 | 7/2004 | Rossen |
| 2004/0167617 A1 | 8/2004 | Voellmicke et al. |
| 2004/0171998 A1 | 9/2004 | Marasco, Jr. |
| 2004/0193218 A1 | 9/2004 | Butler |
| 2004/0241214 A1 | 12/2004 | Kirkwood et al. |
| 2004/0243042 A1 | 12/2004 | Lipman |
| 2005/0015036 A1 | 1/2005 | Lutri et al. |
| 2005/0020955 A1 | 1/2005 | Sanders et al. |
| 2005/0131327 A1 | 6/2005 | Lockwood et al. |
| 2005/0230422 A1 | 10/2005 | Muller et al. |
| 2006/0009744 A1 | 1/2006 | Edrman et al. |
| 2006/0020234 A1 | 1/2006 | Chou et al. |
| 2006/0029650 A1 | 2/2006 | Coffey |
| 2006/0070458 A1 | 4/2006 | Jones et al. |
| 2006/0079599 A1 | 4/2006 | Arthur |
| 2006/0100586 A1 | 5/2006 | Karpowicz |
| 2006/0100597 A1 | 5/2006 | Miskie |
| 2006/0122548 A1 | 6/2006 | Abrams |
| 2006/0161123 A1 | 7/2006 | Kudo et al. |
| 2006/0173514 A1 | 8/2006 | Biel et al. |
| 2006/0206047 A1 | 9/2006 | Lampe et al. |
| 2006/0253082 A1 | 11/2006 | Mcintosh et al. |
| 2006/0273109 A1 | 12/2006 | Keller |
| 2007/0003604 A1 | 1/2007 | Jones |
| 2007/0004896 A1 | 1/2007 | Ito et al. |
| 2007/0009580 A1 | 1/2007 | DiCosmo et al. |
| 2007/0027414 A1 | 2/2007 | Hoffman et al. |
| 2007/0032762 A1 | 2/2007 | Vogel |
| 2007/0032763 A1 | 2/2007 | Vogel |
| 2007/0038172 A1 | 2/2007 | Zamierowski |
| 2007/0040454 A1 | 2/2007 | Freudenberger et al. |
| 2007/0055209 A1 | 3/2007 | Patel et al. |
| 2007/0078467 A1 | 4/2007 | Mullen |
| 2007/0100308 A1 | 5/2007 | Miyairi |
| 2007/0141101 A1 | 6/2007 | Nugent et al. |
| 2007/0147947 A1 | 6/2007 | Stenton et al. |
| 2007/0164047 A1 | 7/2007 | Reidt et al. |
| 2007/0185463 A1 | 8/2007 | Mulligan |
| 2007/0203062 A1 | 8/2007 | Ellis-Behnke et al. |
| 2007/0225663 A1 | 9/2007 | Watt et al. |
| 2007/0260207 A1 | 11/2007 | Ugander et al. |
| 2007/0282236 A1 | 12/2007 | LaGreca |
| 2008/0004549 A1 | 1/2008 | Anderson et al. |
| 2008/0031748 A1 | 2/2008 | Ihle et al. |
| 2008/0058691 A1 | 3/2008 | Sorensen |
| 2008/0060550 A1 | 3/2008 | MacDonald et al. |
| 2008/0089173 A1 | 4/2008 | Lu et al. |
| 2008/0132821 A1 | 6/2008 | Propp et al. |
| 2008/0167592 A1 | 7/2008 | Greer |
| 2008/0200905 A1 | 8/2008 | Heaton |
| 2008/0206155 A1 | 8/2008 | Tamarkin et al. |
| 2008/0208147 A1 | 8/2008 | Argenta et al. |
| 2008/0208163 A1 | 8/2008 | Wilkie |
| 2008/0223378 A1 | 9/2008 | Henderson et al. |
| 2008/0254103 A1 | 10/2008 | Harris et al. |
| 2008/0287880 A1 | 11/2008 | Keller |
| 2008/0294147 A1 | 11/2008 | Radl et al. |
| 2008/0300555 A1 | 12/2008 | Olson et al. |
| 2008/0306407 A1 | 12/2008 | Taylor |
| 2008/0306456 A1 | 12/2008 | Riesinger |
| 2008/0312572 A1 | 12/2008 | Riesinger |
| 2008/0314929 A1 | 12/2008 | Keller |
| 2009/0005746 A1 | 1/2009 | Nielsen et al. |
| 2009/0020561 A1 | 1/2009 | Keller |
| 2009/0022779 A1 | 1/2009 | Kelly et al. |
| 2009/0030086 A1 | 1/2009 | Eady et al. |
| 2009/0036873 A1 | 2/2009 | Nielsen et al. |
| 2009/0054855 A1 | 2/2009 | Blott et al. |
| 2009/0082740 A1 | 3/2009 | Lockwood et al. |
| 2009/0093550 A1 | 4/2009 | Rolfes et al. |
| 2009/0098073 A1 | 4/2009 | MacDonald et al. |
| 2009/0125004 A1 | 5/2009 | Shen et al. |
| 2009/0131892 A1 | 5/2009 | Karpowicz et al. |
| 2009/0134186 A1 | 5/2009 | Keller |
| 2009/0137973 A1 | 5/2009 | Karpowicz et al. |
| 2009/0157017 A1 | 6/2009 | Ambrosio |
| 2009/0157024 A1 | 6/2009 | Song |
| 2009/0196844 A1 | 8/2009 | Choi et al. |
| 2009/0198201 A1 | 8/2009 | Adahan |
| 2009/0204085 A1 | 8/2009 | Biggie et al. |
| 2009/0216170 A1 | 8/2009 | Robinson et al. |
| 2009/0221977 A1 | 9/2009 | Blott et al. |
| 2009/0221990 A1 | 9/2009 | Jaeb et al. |
| 2009/0227935 A1 | 9/2009 | Zanella et al. |
| 2009/0234306 A1 | 9/2009 | Vitaris |
| 2009/0254053 A1 | 10/2009 | Svensby et al. |
| 2009/0270820 A1 | 10/2009 | Johnson |
| 2009/0275872 A1 | 11/2009 | Addison et al. |
| 2009/0275922 A1 | 11/2009 | Coulthard et al. |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299306 A1 | 12/2009 | Buan |
| 2009/0299308 A1 | 12/2009 | Kazala et al. |
| 2009/0299340 A1 | 12/2009 | Kazala et al. |
| 2009/0312723 A1 | 12/2009 | Blott et al. |

(56) References Cited

U.S. PATENT DOCUMENTS

| | | |
|---|---|---|
| 2010/0004611 A1 | 1/2010 | Aali |
| 2010/0016767 A1 | 1/2010 | Jones et al. |
| 2010/0022972 A1 | 1/2010 | Lina et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036305 A1 | 2/2010 | Green |
| 2010/0036334 A1 | 2/2010 | Heagle et al. |
| 2010/0055158 A1 | 3/2010 | Vitaris et al. |
| 2010/0069858 A1 | 3/2010 | Olson |
| 2010/0069863 A1 | 3/2010 | Olson |
| 2010/0084074 A1 | 4/2010 | McClernon et al. |
| 2010/0106112 A1 | 4/2010 | Vogel |
| 2010/0106120 A1 | 4/2010 | Holm |
| 2010/0106121 A1 | 4/2010 | Holm |
| 2010/0121286 A1 | 5/2010 | Locke et al. |
| 2010/0122417 A1 | 5/2010 | Vrzalik et al. |
| 2010/0125234 A1 | 5/2010 | Smith |
| 2010/0125258 A1 | 5/2010 | Coulthard et al. |
| 2010/0150991 A1 | 6/2010 | Bernstein |
| 2010/0159192 A1 | 6/2010 | Cotton |
| 2010/0191196 A1 | 7/2010 | Heagle |
| 2010/0191198 A1 | 7/2010 | Heagle |
| 2010/0196106 A1 | 8/2010 | Allen |
| 2010/0210986 A1 | 8/2010 | Sanders |
| 2010/0217177 A1 | 8/2010 | Cali et al. |
| 2010/0230467 A1 | 9/2010 | Crisuolo et al. |
| 2010/0249733 A9 | 9/2010 | Blott et al. |
| 2010/0259406 A1 | 10/2010 | Caso et al. |
| 2010/0262090 A1 | 10/2010 | Riesinger |
| 2010/0262091 A1 | 10/2010 | Larsson |
| 2010/0280468 A1 | 11/2010 | Haggstrom et al. |
| 2010/0305490 A1 | 12/2010 | Coulthard et al. |
| 2010/0318043 A1 | 12/2010 | Malhi et al. |
| 2010/0318052 A1 | 12/2010 | Ha et al. |
| 2011/0004172 A1 | 1/2011 | Eckstein et al. |
| 2011/0015593 A1 | 1/2011 | Svedman et al. |
| 2011/0021431 A1 | 1/2011 | Jones et al. |
| 2011/0021964 A1 | 1/2011 | Larsen et al. |
| 2011/0028290 A1 | 2/2011 | Ozawa |
| 2011/0028919 A1 | 2/2011 | Johnnison et al. |
| 2011/0028921 A1 | 2/2011 | Hartwell et al. |
| 2011/0033503 A1 | 2/2011 | Sinko et al. |
| 2011/0034888 A1 | 2/2011 | Aali |
| 2011/0034892 A1 | 2/2011 | Buan |
| 2011/0052664 A1 | 3/2011 | Tennican et al. |
| 2011/0054422 A1 | 3/2011 | Locke et al. |
| 2011/0054423 A1 | 3/2011 | Blott et al. |
| 2011/0086077 A1 | 4/2011 | McCrea et al. |
| 2011/0092927 A1 | 4/2011 | Wilkes et al. |
| 2011/0092958 A1 | 4/2011 | Jacobs |
| 2011/0098621 A1 | 4/2011 | Fabo et al. |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0125066 A1 | 5/2011 | Robinson et al. |
| 2011/0130712 A1 | 6/2011 | Topaz |
| 2011/0137222 A1 | 6/2011 | Masini |
| 2011/0172617 A1 | 7/2011 | Riesinger |
| 2011/0178375 A1 | 7/2011 | Forster |
| 2011/0218509 A1 | 9/2011 | Dontas |
| 2011/0224631 A1 | 9/2011 | Simmons |
| 2011/0245682 A1 | 10/2011 | Robinson et al. |
| 2011/0245788 A1 | 10/2011 | Marquez Canada |
| 2011/0247636 A1 | 10/2011 | Pollack |
| 2011/0257572 A1 | 10/2011 | Locke et al. |
| 2011/0295220 A1 | 12/2011 | Heaton et al. |
| 2012/0041402 A1 | 2/2012 | Greener |
| 2012/0051945 A1 | 3/2012 | Orndorff et al. |
| 2012/0065664 A1 | 3/2012 | Avitable et al. |
| 2012/0095380 A1 | 4/2012 | Gergley et al. |
| 2012/0095426 A1 | 4/2012 | Visscher et al. |
| 2012/0101465 A1 | 4/2012 | Mcguire, Jr. |
| 2012/0123311 A1 | 5/2012 | Weidemann-Hendrickson et al. |
| 2012/0123358 A1 | 5/2012 | Hall et al. |
| 2012/0172778 A1 | 7/2012 | Rastegar et al. |
| 2012/0203145 A1 | 8/2012 | Nilsson |
| 2012/0203189 A1 | 8/2012 | Barta et al. |
| 2012/0222687 A1 | 9/2012 | Czajka, Jr. et al. |
| 2012/0232502 A1 | 9/2012 | Lowing |
| 2012/0238932 A1 | 9/2012 | Atteia et al. |
| 2013/0090615 A1 | 4/2013 | Jaeb et al. |
| 2013/0090616 A1 | 4/2013 | Neubauer |
| 2013/0102979 A1 | 4/2013 | Coulthard et al. |
| 2013/0138054 A1 | 5/2013 | Fleischmann |
| 2013/0150814 A1 | 6/2013 | Buan |
| 2013/0165878 A1 | 6/2013 | Heagle |
| 2013/0274688 A1 | 10/2013 | Weston |
| 2013/0296762 A1 | 11/2013 | Toth |
| 2013/0302545 A1 | 11/2013 | Schnelker et al. |
| 2013/0338614 A1 | 12/2013 | Heaton et al. |
| 2014/0114268 A1 | 4/2014 | Auguste et al. |
| 2014/0155849 A1 | 6/2014 | Heaton et al. |
| 2014/0228791 A1 | 8/2014 | Hartwell |
| 2014/0236109 A1 | 8/2014 | Greener |
| 2014/0309601 A1 | 10/2014 | Hall et al. |
| 2015/0065965 A1 | 3/2015 | Haggstrom et al. |
| 2015/0209492 A1 | 7/2015 | Blott et al. |
| 2015/0320604 A1 | 11/2015 | Adie et al. |
| 2016/0051737 A1 | 2/2016 | Joshi et al. |
| 2016/0081859 A1 | 3/2016 | Hartwell |
| 2016/0317357 A1 | 11/2016 | Vitaris et al. |
| 2017/0095598 A1 | 4/2017 | Joshi et al. |
| 2017/0128642 A1 | 5/2017 | Buan |
| 2017/0181896 A1 | 6/2017 | Hartwell |
| 2017/0181897 A1 | 6/2017 | Hartwell |
| 2017/0312407 A1 | 11/2017 | Coulthard et al. |
| 2018/0147091 A1 | 5/2018 | Greener et al. |

FOREIGN PATENT DOCUMENTS

| | | |
|---|---|---|
| CA | 2 653 146 | 9/2009 |
| CA | 2 739 243 | 4/2010 |
| CN | 101385887 A | 3/2009 |
| DE | 847475 | 8/1952 |
| DE | 3 137 839 | 3/1983 |
| DE | 3 032 092 | 10/1984 |
| DE | 34 43 101 | 5/1986 |
| DE | 3 935 818 | 5/1991 |
| DE | 4 012 232 | 10/1991 |
| DE | 90 17 289 | 4/1992 |
| DE | 198 44 355 | 4/2000 |
| DE | 20 2004 017 052 | 7/2005 |
| EP | 0 020 662 | 7/1984 |
| EP | 0 257 916 | 3/1988 |
| EP | 0 340 018 | 11/1989 |
| EP | 0 355 186 | 2/1990 |
| EP | 0 521 434 | 1/1993 |
| EP | 0 541 251 | 5/1993 |
| EP | 0 617 152 | 9/1994 |
| EP | 0 619 105 | 10/1994 |
| EP | 0 858 810 | 8/1998 |
| EP | 0 777 504 | 10/1998 |
| EP | 0 888 141 | 1/1999 |
| EP | 0 782 421 | 7/1999 |
| EP | 0 941 726 | 9/1999 |
| EP | 1 068 451 | 10/1999 |
| EP | 1 007 015 | 6/2000 |
| EP | 1 013 290 | 6/2000 |
| EP | 1 029 585 | 8/2000 |
| EP | 1 169 071 | 10/2000 |
| EP | 1 105 171 | 6/2001 |
| EP | 1 105 180 | 6/2001 |
| EP | 1 107 813 | 6/2001 |
| EP | 1 411 874 | 7/2001 |
| EP | 1 030 657 | 10/2001 |
| EP | 1 283 702 | 11/2001 |
| EP | 1 339 366 | 6/2002 |
| EP | 1 897 569 | 8/2002 |
| EP | 0 708 620 | 5/2003 |
| EP | 1 306 123 | 5/2003 |
| EP | 1 088 569 | 8/2003 |
| EP | 1 565 219 | 12/2003 |

(56) References Cited

FOREIGN PATENT DOCUMENTS

| | | |
|---|---|---|
| EP | 1 440 737 | 7/2004 |
| EP | 1 578 477 | 7/2004 |
| EP | 1 018 967 | 8/2004 |
| EP | 1 452 156 | 9/2004 |
| EP | 1 440 667 | 3/2006 |
| EP | 1 284 777 | 4/2006 |
| EP | 1 807 032 | 5/2006 |
| EP | 0 982 015 | 8/2006 |
| EP | 1 923 077 | 11/2006 |
| EP | 1 904 137 | 1/2007 |
| EP | 1 448 261 | 2/2007 |
| EP | 1 171 065 | 3/2007 |
| EP | 1 922 045 | 3/2007 |
| EP | 1 931 413 | 4/2007 |
| EP | 1 880 840 | 1/2008 |
| EP | 2 059 204 | 1/2008 |
| EP | 1 476 217 | 3/2008 |
| EP | 2 079 507 | 4/2008 |
| EP | 2 106 255 | 7/2008 |
| EP | 1 955 887 | 8/2008 |
| EP | 2 109 472 | 8/2008 |
| EP | 1 121 163 | 11/2008 |
| EP | 2 185 206 | 1/2009 |
| EP | 2 178 573 | 2/2009 |
| EP | 2 203 137 | 4/2009 |
| EP | 2 079 507 | 7/2009 |
| EP | 2 098 257 | 9/2009 |
| EP | 2 244 746 | 9/2009 |
| EP | 2 254 537 | 9/2009 |
| EP | 2 111 804 | 10/2009 |
| EP | 1 985 270 | 12/2009 |
| EP | 1 637 088 | 1/2010 |
| EP | 2 161 011 | 3/2010 |
| EP | 2 326 295 | 3/2010 |
| EP | 2 172 164 | 4/2010 |
| EP | 1 807 031 | 7/2010 |
| EP | 2 253 353 | 11/2010 |
| EP | 2 004 116 | 6/2011 |
| EP | 2 335 749 | 6/2011 |
| EP | 2 349 155 | 8/2011 |
| EP | 1 263 366 | 9/2011 |
| EP | 2 420 214 | 2/2012 |
| EP | 2 021 046 | 3/2012 |
| EP | 2 462 908 | 6/2012 |
| EP | 2 021 047 | 10/2013 |
| EP | 2 711 034 | 3/2014 |
| EP | 2 305 325 | 4/2014 |
| EP | 2 345 437 | 4/2014 |
| EP | 2 687 245 | 9/2014 |
| EP | 2 544 642 | 1/2015 |
| EP | 2 648 668 | 1/2015 |
| EP | 2 931 197 | 10/2015 |
| EP | 3 085 344 | 10/2016 |
| EP | 3 139 878 | 3/2017 |
| FR | 1 163 907 | 10/1958 |
| GB | 114754 | 4/1918 |
| GB | 236350 | 7/1925 |
| GB | 641061 | 8/1950 |
| GB | 821959 | 10/1959 |
| GB | 1224009 | 3/1971 |
| GB | 1255395 | 12/1971 |
| GB | 1400124 | 7/1975 |
| GB | 1549756 | 8/1979 |
| GB | 2099306 | 12/1982 |
| GB | 2195255 | 4/1988 |
| GB | 2288734 | 11/1995 |
| GB | 2307180 | 5/1997 |
| GB | 2378392 | 2/2003 |
| GB | 2415908 | 1/2006 |
| GB | 2424582 | 10/2006 |
| GB | 2435419 | 2/2007 |
| GB | 2435422 | 8/2007 |
| JP | 59-87824 | 6/1984 |
| JP | H02-139624 | 11/1990 |
| JP | H09-505752 | 6/1997 |
| JP | 2001-011759 | 1/2001 |
| JP | 2003-165843 | 6/2003 |
| JP | 2003-250879 | 9/2003 |
| JP | 2003-532504 | 11/2003 |
| JP | 2004-509658 | 4/2004 |
| JP | 2009-506878 | 2/2009 |
| JP | 2009-509570 | 3/2009 |
| JP | 2009-536852 | 10/2009 |
| JP | 2010-504816 | 2/2010 |
| JP | 2010-516387 | 5/2010 |
| JP | 2014-518651 | 3/2014 |
| SU | 1251912 A1 | 4/1983 |
| WO | WO 1983/00742 | 3/1983 |
| WO | WO 1984/01904 | 5/1984 |
| WO | WO 1990/11795 | 10/1990 |
| WO | WO 1991/00718 | 1/1991 |
| WO | WO 1992/009301 | 6/1992 |
| WO | WO 1992/09651 | 6/1992 |
| WO | WO 1992/20299 | 11/1992 |
| WO | WO 1993/06802 | 4/1993 |
| WO | WO 1993/09176 | 5/1993 |
| WO | WO 1994/020133 | 9/1994 |
| WO | WO 1994/23677 | 10/1994 |
| WO | WO 1995/04511 | 2/1995 |
| WO | WO 1995/14451 | 6/1995 |
| WO | WO 1995/16416 | 6/1995 |
| WO | WO 1995/29959 | 11/1995 |
| WO | WO 1996/05873 | 2/1996 |
| WO | WO 1996/21410 | 7/1996 |
| WO | WO 1996/40174 | 12/1996 |
| WO | WO 1997/03717 | 2/1997 |
| WO | WO 1997/11658 | 4/1997 |
| WO | WO 1997/33922 | 9/1997 |
| WO | WO 1997/42986 | 11/1997 |
| WO | WO 1998/03267 | 1/1998 |
| WO | WO 1998/06444 | 2/1998 |
| WO | WO 1999/01173 | 1/1999 |
| WO | WO 1999/17698 | 4/1999 |
| WO | WO 1999/30629 | 6/1999 |
| WO | WO 1999/39671 | 8/1999 |
| WO | WO 1999/047097 | 9/1999 |
| WO | WO 1999/65536 | 12/1999 |
| WO | WO 2000/07653 | 2/2000 |
| WO | WO 2000/38752 | 7/2000 |
| WO | WO 2000/42957 | 7/2000 |
| WO | WO 2000/50143 | 8/2000 |
| WO | WO 2000/59424 | 10/2000 |
| WO | WO 2000/61206 | 10/2000 |
| WO | WO 2000/62827 | 10/2000 |
| WO | WO 2000/064396 | 11/2000 |
| WO | WO 2001/19430 | 3/2001 |
| WO | WO 2001/34223 | 5/2001 |
| WO | WO 2001/062312 | 8/2001 |
| WO | WO 2001/066017 | 9/2001 |
| WO | WO 2001/085248 | 11/2001 |
| WO | WO 2002/02079 | 1/2002 |
| WO | WO 2002/17840 | 3/2002 |
| WO | WO 2002/26180 | 4/2002 |
| WO | WO 2002/38096 | 5/2002 |
| WO | WO 2002/076379 | 10/2002 |
| WO | WO 2002/083046 | 10/2002 |
| WO | WO 2002/092783 | 11/2002 |
| WO | WO 2002/094256 | 11/2002 |
| WO | WO 2002/102864 | 12/2002 |
| WO | WO 2003/045492 | 6/2003 |
| WO | WO 2003/057307 | 7/2003 |
| WO | WO 2004/024300 | 3/2004 |
| WO | WO 2004/037334 | 5/2004 |
| WO | WO 2004/054632 | 7/2004 |
| WO | WO 2004/073566 | 9/2004 |
| WO | WO 2004/077387 | 9/2004 |
| WO | WO 2003/092620 | 12/2004 |
| WO | WO 2005/009488 | 2/2005 |
| WO | WO 2005/016179 | 2/2005 |
| WO | WO 2005/017000 | 2/2005 |
| WO | WO 2005/018695 | 3/2005 |
| WO | WO 2005/025447 | 3/2005 |
| WO | WO 2005/025666 | 3/2005 |
| WO | WO 2005/046761 | 5/2005 |

(56) References Cited

FOREIGN PATENT DOCUMENTS

| | | |
|---|---|---|
| WO | WO 2005/051461 | 6/2005 |
| WO | WO 2005/070480 | 8/2005 |
| WO | WO 2005/082435 | 9/2005 |
| WO | WO 2005/105180 | 11/2005 |
| WO | WO 2005/118011 | 12/2005 |
| WO | WO 2005/123170 | 12/2005 |
| WO | WO 2006/014534 | 2/2006 |
| WO | WO 2006/030054 | 3/2006 |
| WO | WO 2006/034128 | 3/2006 |
| WO | WO 2006/048246 | 5/2006 |
| WO | WO 2006/052745 | 5/2006 |
| WO | WO 2006/052839 | 5/2006 |
| WO | WO 2006/056294 | 6/2006 |
| WO | WO 2006/081403 | 8/2006 |
| WO | WO 2006/087021 | 8/2006 |
| WO | WO 2006/116992 | 11/2006 |
| WO | WO 2006/135506 | 12/2006 |
| WO | WO 2007/002835 | 1/2007 |
| WO | WO 2007/013064 | 2/2007 |
| WO | WO 2007/019038 | 2/2007 |
| WO | WO 2007/024230 | 3/2007 |
| WO | WO 2007/030598 | 3/2007 |
| WO | WO 2007/030601 A2 | 3/2007 |
| WO | WO 2007/084792 | 7/2007 |
| WO | WO 2007/085396 | 8/2007 |
| WO | WO 2007/092397 | 8/2007 |
| WO | WO 2007/106592 | 9/2007 |
| WO | WO 2007/106594 | 9/2007 |
| WO | WO 2007/124198 | 11/2007 |
| WO | WO 2007/133618 | 11/2007 |
| WO | WO 2008/013896 | 1/2008 |
| WO | WO 2008/027449 | 3/2008 |
| WO | WO 2008/039223 | 4/2008 |
| WO | WO 2008/039314 | 4/2008 |
| WO | WO 2008/039839 | 4/2008 |
| WO | WO 2008/040020 | 4/2008 |
| WO | WO 2008/041926 | 4/2008 |
| WO | WO 2008/049277 | 5/2008 |
| WO | WO 2008/064502 | 6/2008 |
| WO | WO 2008/076407 | 6/2008 |
| WO | WO 2008/082444 | 7/2008 |
| WO | WO 2008/100437 | 8/2008 |
| WO | WO 2008/100440 | 8/2008 |
| WO | WO 2008/104609 | 9/2008 |
| WO | WO 2008/112304 | 9/2008 |
| WO | WO 2008/131895 | 11/2008 |
| WO | WO 2008/134544 | 11/2008 |
| WO | WO 2008/134774 | 11/2008 |
| WO | WO 2009/002260 | 12/2008 |
| WO | WO 2009/019227 | 2/2009 |
| WO | WO 2009/019229 | 2/2009 |
| WO | WO 2009/021523 | 2/2009 |
| WO | WO 2009/146441 | 3/2009 |
| WO | WO 2009/042514 | 4/2009 |
| WO | WO 2009/047524 | 4/2009 |
| WO | WO 2009/052193 | 4/2009 |
| WO | WO 2009/060327 | 5/2009 |
| WO | WO 2009/062327 | 5/2009 |
| WO | WO 2009/066104 | 5/2009 |
| WO | WO 2009/066105 | 5/2009 |
| WO | WO 2009/066106 | 5/2009 |
| WO | WO 2009/071932 | 6/2009 |
| WO | WO 2009/089390 | 7/2009 |
| WO | WO 2009/097534 | 8/2009 |
| WO | WO 2009/103031 | 8/2009 |
| WO | WO 2009/111655 | 9/2009 |
| WO | WO 2009/111657 | 9/2009 |
| WO | WO 2009/114790 | 9/2009 |
| WO | WO 2009/117635 | 9/2009 |
| WO | WO 2009/122989 | 10/2009 |
| WO | WO 2009/124100 | 10/2009 |
| WO | WO 2009/124125 | 10/2009 |
| WO | WO 2009/126102 | 10/2009 |
| WO | WO 2009/126103 | 10/2009 |
| WO | WO 2009/126833 | 10/2009 |
| WO | WO 2009/146441 | 12/2009 |
| WO | WO 2009/151380 | 12/2009 |
| WO | WO 2009/156709 | 12/2009 |
| WO | WO 2009/158124 | 12/2009 |
| WO | WO 2009/158127 | 12/2009 |
| WO | WO 2009/158128 | 12/2009 |
| WO | WO 2009/158130 | 12/2009 |
| WO | WO 2010/008167 | 1/2010 |
| WO | WO 2010/026251 | 3/2010 |
| WO | WO 2010/033574 | 3/2010 |
| WO | WO 2010/033613 | 3/2010 |
| WO | WO 2010/035017 | 4/2010 |
| WO | WO 2010/051418 | 5/2010 |
| WO | WO 2010/059849 | 5/2010 |
| WO | WO 2010/072309 | 7/2010 |
| WO | WO 2010/072395 | 7/2010 |
| WO | WO 2010/082872 | 7/2010 |
| WO | WO 2010/089448 | 8/2010 |
| WO | WO 2010/120776 | 10/2010 |
| WO | WO 2010/139926 | 12/2010 |
| WO | WO 2010/141271 | 12/2010 |
| WO | WO 2010/142959 | 12/2010 |
| WO | WO 2010/147533 | 12/2010 |
| WO | WO 2010/147592 | 12/2010 |
| WO | WO 2011/019476 | 2/2011 |
| WO | WO 2011/023275 | 3/2011 |
| WO | WO 2011/023650 | 3/2011 |
| WO | WO 2011/115908 | 9/2011 |
| WO | WO 2011/128651 | 10/2011 |
| WO | WO 2011/135284 | 11/2011 |
| WO | WO 2011/135285 | 11/2011 |
| WO | WO 2011/135286 | 11/2011 |
| WO | WO 2011/135287 | 11/2011 |
| WO | WO 2011/144888 | 11/2011 |
| WO | WO 2012/009370 | 1/2012 |
| WO | WO 2012/022484 | 2/2012 |
| WO | WO 2012/028842 | 3/2012 |
| WO | WO 2012/041296 | 4/2012 |
| WO | WO 2012/074512 | 6/2012 |
| WO | WO 2012/131237 | 10/2012 |
| WO | WO 2012/140378 | 10/2012 |
| WO | WO 2012/143665 | 10/2012 |
| WO | WO 2012/146656 | 11/2012 |
| WO | WO 2012/150235 | 11/2012 |
| WO | WO 2015/172108 | 11/2015 |

OTHER PUBLICATIONS

Argenta, Louis C., et al., "Vacuum-Assisted Closure: A New Method for Wound Control and Treatment; Clinical Experience", Ann Plas Surg 1997;38:563-577 (Dec. 10, 1996).

Aubrey, D.A. et al., "Treatment of the Perineal Wound after Proctectomy by Intermittent Irrigation", Arch. Surg., vol. 119, Oct. 1984, pp. 1141-1144.

Bagautdinov, N.A., "Variant of External Vacuum Aspiration in the Treatment of Purulent Diseases of Soft Tissues", in Current Problems in Modern Clinical Surgery: Interdepartmental Collection, edited by V. Ye. Volkov et al. (Chuvash State University, Cheboksary, USSR 1986) pp. 94-96.

Canadian Office Action, re CA Application No. 2739605, dated Aug. 22, 2011.

Chariker, M.E. et al., "Effective Management of Incisional and Cutaneous Fistulae with Closed Suction Wound Drainage", Contemporary Surgery, vol. 34, Jun. 1989, pp. 59-63.

Chintamani, et al., "Half versus full vacuum suction drainage after modified radical mastectomy for breast cancer—a prospective randomized clinical trial", Research Article (Jan. 27, 2005), 1-5.

Communication of Notice of Opposition dated Dec. 17, 2015, and Opposition of European patent EP 2563308 B1, dated Dec. 11, 2015, on behalf of KCI Licensing, Inc., and publications D1-D6, in 250 pages.

Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.

(56) References Cited

OTHER PUBLICATIONS

Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y., et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Hartz, R.S. et al., Healing of the Perineal Wound, Arch. Surg., Apr. 1980, 115, 471-474.
Health Technology, Literature R., "Vacuum Assisted Closure Therapy for Wound Care", Health Technology Literature Review, Dec. 2004, pp. 3-59.
International Search Report, re PCT Application No. PCT/GB2008/051088, dated Mar. 4, 2009.
International Search Report, re PCT Application No. PCT/GB2008/051090, dated Mar. 4, 2009.
International Search Report, re PCT Application No. PCT/GB2008/051089, dated Mar. 4, 2009.
International Search Report for International Application No. PCT/GB2011/000622, dated Jul. 28, 2011.
International Search Report for International Application No. PCT/GB2011/000625, dated Aug. 10, 2011 in 5 pages.
International Search Report for PCT Application No. PCT/GB2011/000626, dated Aug. 4, 2011.
International Search Report for PCT Application No. PCT/GB2011/000628, dated Sep. 6, 2012.
International Search Report for International Application No. PCT/GB2011/000621, dated Jul. 26, 2011.
International Search Report for International Application No. PCT/GB2011/000629, dated Dec. 23, 2011.
Kalypto Medical, NPD 1000 Negative Pressure Wound Care System, Clinician & Patient Instructions for Use (publication date unknown, believed to be Feb. 2010).
Kalypto Medical, NPD 1000 Product Brochure (publication date unknown, believed to be Nov. 2010).
Kendall ULTEC Hydrocolloid Dressing (4"×4"), product ordering page, web page downloaded Jul. 13, 2014.
Khirugii, Vestnik, "A Collection of Published Studies Complementing the Research and Innovation of Wound Care", The Kremlin Papers, Perspectives in Wound Care, Russian Medical Journal, Vestnik Khirurgii, Blue Sky Publishing (2004), 2-17.
Kostiuchenok, B. M. et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California, 2004, pp. 3-4 (English translation only).
Membrane Filters, in 17 pages, from website: http://www.advantecmfs.com/catalog/filt/membrane.pdf#page=11 (date unknown, but believed to be copyright 2001-2011).
Morykwas, M. et al., "Vacuum-Assisted Closure: A New Method for Wound Control and Treatment: Animal Studies and Basic Foundation", Annals Plastic Surgery, vol. 38, No. 6, Jun. 1997, pp. 553-562 (Dec. 10, 1996).
NURSING75, Wound Suction: Better Drainage with Fewer Problems, Nursing, vol. 5, No. 10, Oct. 1975, pp. 52-55.
Prevena™ Incision Management System, Clinician Guide, pp. 1-9, Jan. 2010.
Prevena™ Incision Management System, Patient Guide, pp. 1-2, Jan. 2010.
Protz, Kerstin: "Modern Wundauflagen unterstutzen Heilungsprozess", Wundversorgung: Indikation und Anwendung, Geriatrie Journal, Apr. 2005, pp. 3333-3339, with translation.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, J., "World Wide Wounds—Next Generation of Products for Wound Management", 2002, in 13 pages.
Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers", The Lancet, Sep. 1983, pp. 532-534.
Svedman, P., "A Dressing Allowing Continuous Treatment of a Biosurface", IRCS Med. Science: Biomed. Tech.; Clinic. Med.; Surg. and Transplantation, 1979, 7, p. 221.
Svedman, P. et al., "A Dressing System Providing Fluid Supply and Suction Drainage Used for Continuous or Intermittent Irrigation", Annals of Plastic Surgery, vol. 17, No. 2, Aug. 1986, pp. 125-133.
Swift, et al, "Quorum Sensing in *Aeromonas hydrophila* and *Aeromonas salmonicida*: Identification of LuxRI Homologs AhyRI and AsaRI and Their Cognate N-Acylhomoserine Lactone Signal Molecules," J. Bacteriol., 179(17):5271-5281 (1997).
Teder, H. et al., "Continuous Wound Irrigation in the Pig," Journal of Investigative Surgery, vol. 3, 1990, pp. 399-407.
The American Heritage Dictionary of the English Language, Fourth Edition, 2000.
Tribble, D. E., "An Improved Sump Drain-Irrigation Device of Simple Construction", Archives of Surgery New York, vol. 105, Sep. 1972, in 4 pages.
Usupov, Y. N., et al., "Active Wound Drainage", The Kremlin Papers: Perspectives in Wound Care, Russian Journal: Vestnik Khirurgii, BlueSky Publishing, La Costa, California (2004), pp. 8-10.
Venturi, Mark L., "Mechanisms and Clinical Applications of the Vacuum-Assisted Closure (VAC) Device", Am J Clin Dermatol (2005) 693, 185-194; Review Article (2005),185-194.
Vijanto, J. and J. Raekallio, Local Hyperalimentation of Open Wounds, Br. J. surg., 1976, 63, 427-430.
Webb, New Techniques in Wound Management: Vacuum-Assisted Wound Closure, Journal of the American Academy of Orthopadic Surgeons, vol. 10, No. 5, Sep. 2002, pp. 303-311.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.
Declaration of Chris Locke submitted in the Opposition against European Patent No. EP 2 563 308, dated Sep. 7, 2016, in 6 pages.
Smith & Nephew, "PICO Single Use Negative Pressure Wound Therapy System", spiral booklet, Mar. 2011, in 7 pages.
"Technology Watch", May 1989, in 1 page.
Bevan, D. et al., "Diverse and potent activities of HGF/SF in skin wound repair", Journal of Pathology, vol. 203, 2004, pp. 831-838, in 8 pages.
English Translation of Invalidity Suit by KCI Medizinprodukte GmbH versus Kalypto Medical, Inc., concerning declaration of invalidity of the German part of the European Patent No. 2 021 046 (German application No. 60 2007 021 330.4) dated Mar. 11, 2015 in 38 pages. EP 2 021 046 is related to the present application by virtue of a common priority claim to U.S. Appl. No. 11/432,855, now U.S. Pat. No. 7,615,036, and U.S. Appl. No. 11/610,458, now U.S. Pat. No. 7,779,625.
Hersle, K. et al., "Uses of Dextranomer Absorbent Pads After Cryosurgery of Cutaneous Malignancies", The Journal of Dermatologic Surgery and Oncology, vol. 8, Jan. 1982, in 4 pages.
Mitchell, R. et al., "Role of Stem Cells in Tissue Homeostasis", Pocket Companion to Robbins and Cotran Pathologic Basis of Disease, 7th Edition, 2006.
Reply to Appeal, in Opposition by KCI Licensing Inc. to Smith & Nephew PLC, re European Patent No. 2 563 308, dated May 24, 2018, in 9 pages.

(56) References Cited

OTHER PUBLICATIONS

Reply to Grounds of Appeal, in Opposition by KCI Licensing Inc. to Smith & Nephew PLC, re European Patent No. 2 563 308, dated Apr. 27, 2018, in 4 pages.

* cited by examiner

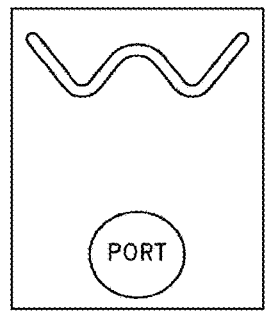
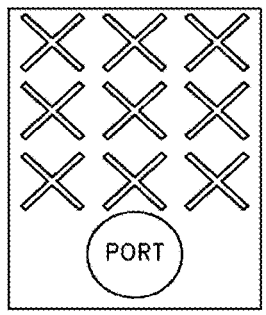
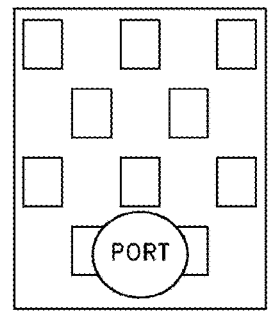
*FIG. 14G*  *FIG. 14H*  *FIG. 14I*
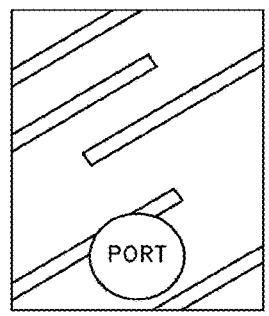
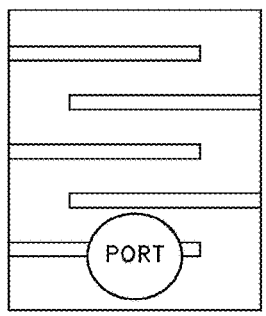
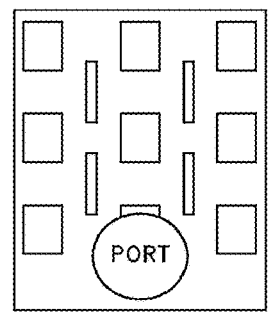
*FIG. 14J*  *FIG. 14K*  *FIG. 14L*

WOUND DRESSING AND METHOD OF USE

CROSS-REFERENCE TO RELATED APPLICATIONS

This application is a continuation of U.S. patent application Ser. No. 14/715,399, filed on May 18, 2015 and published as US 2015/0320604 A1, which is a continuation of U.S. patent application Ser. No. 13/092,042, filed on Apr. 21, 2011, now U.S. Pat. No. 9,061,095, which claims priority to Great Britain Patent Application No. 1006986.2, filed Apr. 27, 2010; Great Britain Patent Application No. 1006983.9, filed Apr. 27, 2010; Great Britain Patent Application No. 1006985.4, filed Apr. 27, 2010; Great Britain Patent Application No. 1006988.8, filed Apr. 27, 2010; and Great Britain Patent Application No. 1008347.5, filed May 19, 2010; all of which are hereby incorporated by reference in their entirety.

BACKGROUND OF THE INVENTION

Field of the Invention

Embodiments of the present invention relate to methods and apparatuses for dressing and treating a wound with topical negative pressure (TNP) therapy. In particular, but not exclusively, embodiments disclosed herein relate to a wound dressing for providing protection to a wound site, in which the wound dressing acts as a buffer to help prevent compression or shear forces exerted on the wound dressing, for example due to patient movement, from harming a healing wound. Embodiments of the wound dressing may act as a waste canister to collect and store wound exudate removed from a wound site, and also relate to the management of solid build-up in a wound dressing covering a wound site whilst TNP therapy is applied. Further, embodiments disclosed herein relate to a method and suction port for applying negative pressure to a wound dressing and a method of manufacturing a suction port and wound dressing.

Description of the Related Art

Many different types of wound dressing are known for aiding in the healing process of a human or animal. These different types of wound dressing include many different types of materials and layers, for example, gauze, pads, foam pads or multi-layer wound dressings.

In addition, TNP therapy, sometimes referred as vacuum assisted closure or negative pressure wound therapy, has recently been proposed as a successful mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema; encouraging blood flow; stimulating the formation of granulation tissue; removing excess exudates and may reduce bacterial load and thus, infection to the wound. Furthermore, TNP therapy permits less outside disturbance of the wound and promotes more rapid healing.

During TNP therapy, a suction source such as a vacuum pump or the like is utilized to create a negative pressure region. That is to say, a region where an experienced pressure is below that of the surroundings. Wound exudate and other potentially harmful material is extracted from the wound region and must be stored for later disposal. A problem associated with many known techniques is that a separate canister must be provided for storage of such exudate. Provision of such canisters is costly and bulky and prone to failure.

A proposal has been suggested to store extracted wound exudate in the wound dressing itself that is used to cover a wound site and create the wound chamber region where negative pressure is established. However, it is known that many different wound types can exude high flow rates of exudate and therefore storage of exuding material in a wound dressing can be problematical since the wound dressing will only have a limited capacity for fluid uptake before a dressing change is required. This can limit a time of use between dressing changes and can prove costly if many wound dressings are required to treat a given wound.

It has been suggested as a solution to this problem, that a liquid impermeable moisture vapor permeable cover layer can be utilized as an uppermost cover layer for the wound dressing. The air impermeable nature of the cover layer provides a sealing layer over the wound site so that negative pressure can be established below the dressing in the region of the wound. The moisture vapor permeability of this covering layer is selected so that liquid can constantly evaporate away from the top of the dressing. This means that as therapy is continued the dressing does not have to take up and hold all liquid exuding from the wound. Rather, some liquid is constantly escaping in the form of moisture vapor from the upper environs of the dressing.

Whilst such dressings work well in practice, the continuous evaporation of moisture vapor from the dressing can lead to the problem of crust formation in the dressing. That is to say, because of the continuous drawing of liquid away from the wound site solid particulate matter is more prone to formation and accumulation in the dressing. Under certain circumstances the build-up of such solid material can lead to blockages forming in the wound dressing in the flowpath between the wound and the source of negative pressure. This can potentially cause problems in that therapy may need to be halted to change a dressing if the blockages reach a critical level.

Further, there is much prior art available relating to the provision of apparatuses and methods of use thereof for the application of TNP therapy to wounds together with other therapeutic processes intended to enhance the effects of the TNP therapy.

It will be appreciated that from time to time accidents may happen to patients undergoing negative pressure wound therapy. Such accidents might cause short term or long term forces to be applied to a dressing covering a wound. Alternatively patient movement may bring the patient and any dressing covering a healing wound into contact with an external object. In such occurrences compressive forces or lateral forces may occur. Such force can cause disturbance of a wound bed which can damage a wound site. A particular cause for concern is during the treatment of skin graft wounds. Under such conditions lateral forces can entirely upset or tear apart a healing skin graft region.

SUMMARY OF THE INVENTION

It is an aim of certain embodiments of the present invention to at least partly mitigate the above-mentioned problems.

It is an aim of certain embodiments of the present invention to provide a method for providing negative pressure at a wound site to aid in wound closure and healing in which wound exudate drawn from a wound site during the therapy is collected and stored in a wound dressing.

It is an aim of certain embodiments of the present invention to provide a wound dressing having an increased capacity for absorbing wound exudate reducing the frequency with which the dressings must be changed.

It is further an aim of certain embodiments of the invention to manage the movement of wound exudate through a dressing to avoid blockages occurring that lead to reduced life of the dressing.

It is an aim of certain embodiments of the present invention to provide a wound dressing having an increased capacity to absorb compressive forces exerted on the wound dressing.

It is an aim of certain embodiments of the present invention to provide a wound dressing having an increased capacity to prevent shear forces from an outer surface of a wound dressing from being translated into corresponding shear forces at a wound site.

It is an aim of certain embodiments of the present invention to provide a wound dressing which can "give" in a direction perpendicular to and parallel to a wound site surface even when the dressing experiences negative pressure.

It is an aim of certain embodiments of the present invention to provide a wound dressing able to be used with topical negative pressure therapy which helps maintain an open flow path so that therapy can be continued unhindered by blockages caused by build-up of solid matter.

It is an aim of certain embodiments of the present invention to provide a method and apparatus for treating a wound with topical negative pressure therapy by preventing blockage of a flowpath region of a wound dressing.

Embodiments disclosed herein are directed toward the treatment of wounds with TNP. In particular, certain embodiments disclose a wound dressing capable of absorbing and storing wound exudate in conjunction with a pump, for example a miniaturized pump. Some wound dressing embodiments further comprise a transmission layer configured to transmit wound exudates to an absorbent layer disposed in the wound dressing. Additionally, some embodiments provide for a port or other fluidic connector configured to retain wound exudate within the wound dressing while transmitting negative pressure to the wound dressing.

According to a first embodiment of the present invention there is provided a wound treatment apparatus comprising:
a wound dressing comprising:
  a transmission layer comprising a 3D knitted or fabric material configured to remain open upon application of negative pressure to the wound dressing;
  an absorbent layer for absorbing wound exudate, the absorbent layer overlying the transmission layer;
  a cover layer overlying the absorbent layer and comprising an orifice,
  wherein the cover layer is moisture vapor permeable;
a pump; and
a suction port for applying negative pressure to the wound dressing for the application of topical negative pressure at a wound site, the suction port comprising:
  a connector portion for connecting the suction port to the pump;
  a sealing surface for sealing the suction port to the cover layer of the wound dressing; and
  a liquid impermeable gas permeable filter element arranged to prevent a liquid from entering the connector portion.

According to a second embodiment of the present invention there is provided a method for the treatment of a wound comprising:
providing a wound dressing comprising:
  a transmission layer comprising a 3D knitted or fabric material;
  an absorbent layer for absorbing wound exudate, the absorbent layer overlying the transmission layer;
  a cover layer overlying the absorbent layer and comprising an orifice,
  wherein the cover layer is moisture vapor permeable;
positioning the dressing over a wound site to form a sealed cavity over the wound site; and
applying negative pressure to the wound site to draw fluid through the transmission layer into the absorbent layer.

According to a another embodiment of the present invention there is provided a wound dressing for providing protection at a wound site, comprising:
a transmission layer comprising a first surface and a further surface spaced apart from the first surface by a relax distance in a relaxed mode of operation; and
a plurality of spacer elements extending between the first and further surfaces and, in a forced mode of operation, locatable whereby the first and further surfaces are spaced apart by a compression distance less than the relax distance.

According to a one embodiment of the present invention there is provided a method for providing protection at a wound site, comprising:
locating a wound dressing comprising a transmission layer over a wound site; and
responsive to a force on the wound dressing, displacing a plurality of spacer elements extending between a first surface and a further surface of the transmission layer whereby;
a distance between the first and further surfaces is reduced as the spacer elements are displaced.

According to another embodiment of the present invention there is provided an apparatus for dressing a wound for the application of topical negative pressure at a wound site, comprising:
a liquid and gas permeable transmission layer;
an absorbent layer for absorbing wound exudate, the absorbent layer overlying the transmission layer;
a gas impermeable cover layer overlying the absorbent layer and comprising a first orifice, wherein the cover layer is moisture vapor permeable.

According to a further embodiment of the present invention there is provided a method of applying TNP at a wound site, comprising the steps of:
applying negative pressure at an orifice of a cover layer of a wound dressing, a peripheral region around the wound site being sealed with the wound dressing, such that air and wound exudate are drawn towards the orifice;
collecting wound exudate, drawn from the wound site, through a transmission layer of the wound dressing, in an absorbent layer of the wound dressing; and
transpiring a water component of the wound exudate collected in the absorbent layer through the cover layer of the wound dressing.

According to an additional embodiment of the present invention there is provided apparatus for dressing a wound for the application of topical negative pressure at a wound site, comprising:
a liquid and gas permeable transmission layer;
an absorbent layer for absorbing wound exudate;
a gas impermeable cover layer overlying the absorbent layer and the transmission layer, the cover layer comprising an orifice connected to the transmission layer; and at least one element configured to reduce the rate at which wound exudate moves towards the orifice when a negative pressure is applied at the orifice.

According to another embodiment of the present invention there is provided a method of applying TNP at a wound site, comprising the steps of:
applying negative pressure at an orifice of a cover layer of a wound dressing, a peripheral region around the wound site being sealed with the wound dressing such that air and wound exudate move towards the orifice;
collecting wound exudate, from the wound site, through a transmission layer of the wound dressing, in an absorbent layer of the wound dressing; and
reducing the rate at which wound exudate moves towards the orifice.

According to still another embodiment of the present invention there is provided apparatus for dressing a wound for the application of topical negative pressure at a wound site, comprising:
an absorbent layer for absorbing wound exudate;
a gas impermeable cover layer overlying the absorbent layer the cover layer comprising at least one orifice configured to allow negative pressure to be communicated through the cover layer in at least two spaced apart regions.

According to an additional embodiment of the present invention there is provided a method of applying TNP at a wound site, comprising the steps of:
sealing a cover layer of a wound dressing around the wound site;
applying negative pressure at at least one orifice in the cover layer, said at least one orifice configured to allow negative pressure to be communicated through the cover layer in at least two spaced apart regions; and
collecting wound exudate, from the wound site, in an absorbent layer of the wound dressing.

According to one embodiment of the present invention there is provided a suction port for applying negative pressure to a wound dressing for the application of topical negative pressure at a wound site, the suction port comprising:
a connector portion for connecting the suction port to a source of negative pressure;
a sealing surface for sealing the suction port to a cover layer of a wound dressing; and
a liquid impermeable gas permeable filter element arranged to prevent a liquid entering the connector portion.

According to an additional embodiment of the present invention there is provided a method of communicating negative pressure to a wound dressing for the application of topical negative pressure at a wound site, comprising the steps of:
applying negative pressure at a connecting portion of a suction port sealed around a perimeter of an orifice in a cover layer of the wound dressing;
filtering gas drawn from within the wound dressing through a liquid impermeable gas permeable filter element of the suction port.

According to another embodiment of the invention there is provided a method of manufacturing a suction port for applying negative pressure to a wound dressing for the application of topical negative pressure at a wound site, the suction port having a connector portion for connecting the suction port to a source of negative pressure and a sealing surface for sealing the suction port to a cover layer of a wound dressing, the method comprising:
disposing a liquid impermeable gas permeable filter element of the suction port at a location to prevent a liquid entering the connector portion.

According to yet another embodiment of the present invention there is provided apparatus for the application of TNP therapy to a wound site, comprising:
a first layer comprising a plurality of openings each having a first open area;
a further layer spaced apart from the first layer comprising a plurality of further openings each having a further open area; and
an air impermeable, moisture vapor permeable cover layer over the first and further layers; wherein
a region between the first and further layers comprises a portion of a flow path for air and/or wound exudate flowing from a wound site and said first open area is less than said further open area.

According to still another embodiment of the present invention there is provided a method of applying TNP therapy to a wound site, comprising:
via a vacuum pump in fluid communication with a wound dressing located over a wound site, applying a negative pressure at the wound site; and
as liquid evaporates through a cover layer of the dressing, preventing blockage of a fluid flowpath region of the wound dressing.

Certain embodiments provide a wound dressing which even when under negative pressure conditions is able to provide further "give" to buffer compression forces from harming a wound.

Certain embodiments provide a wound dressing able to disconnect shear forces applied to the dressing from the wound site covered by the dressing. As a result damage to the wound can be wholly or at least partially avoided.

Certain embodiments provide the advantage that a wound site can be covered with a wound dressing which is simultaneously able to deliver negative pressure wound therapy to a wound site, collect exudate and provide protection from forces operating on the dressing.

Certain embodiments provide the advantage that forces operating on a dressing can be offset by dissipating loads operating over a relatively small distance on an upper layer of the dressing to a relatively larger area on a lower surface of the dressing. The force is thus dissipated over a larger area thus reducing the effect of the force.

Certain embodiments provide the advantage that a wound dressing can be used to collect wound exudate generated during a negative pressure therapy process, whilst extending the useful lifetime of the dressing by transpiring a water component of the wound exudate. A pump remote from the wound dressing can be connected to the wound dressing and reused whilst the wound dressing itself is used to collect wound exudate and may then be disposed of after use.

Certain embodiments provide a wound dressing and/or method of applying topical negative pressure in which a flowpath through a wound dressing is kept open so that therapy can be continued for as long as desired by a care giver.

Certain embodiments prevent solid material, which may cause a blockage, from entering a flowpath region in the wound dressing by using a layer of the dressing to act as a bar to such material.

Certain embodiments prevent build-up of solid material in a flowpath region of a wound dressing by ensuring that any solid material that enters into that flowpath region can always escape into a further region of the dressing.

Certain embodiments provide the advantage that the build-up of solid material in a flowpath in a wound dressing is avoided by having an absorbent layer close to the flowpath region store liquid over time. This helps keep the environment of the flowpath region moist which helps avoid crusting.

Certain embodiments provide the advantage that a wound dressing can be used to collect wound exudate generated during a negative pressure therapy process, whilst extending the useful lifetime of the dressing by transpiring a water component of the wound exudate. A pump remote from the wound dressing can be connected to the wound dressing and reused whilst the wound dressing itself is used to collect wound exudate and may then be disposed of after use.

BRIEF DESCRIPTION OF THE DRAWINGS

Embodiments of the present invention will now be described hereinafter, by way of example only, with reference to the accompanying drawings in which:

FIGS. 14A-L illustrate a range of exemplifying configurations of baffle elements in a wound dressing.

In the drawings like reference numerals refer to like parts.

DETAILED DESCRIPTION OF THE PREFERRED EMBODIMENTS

Figure 1A:
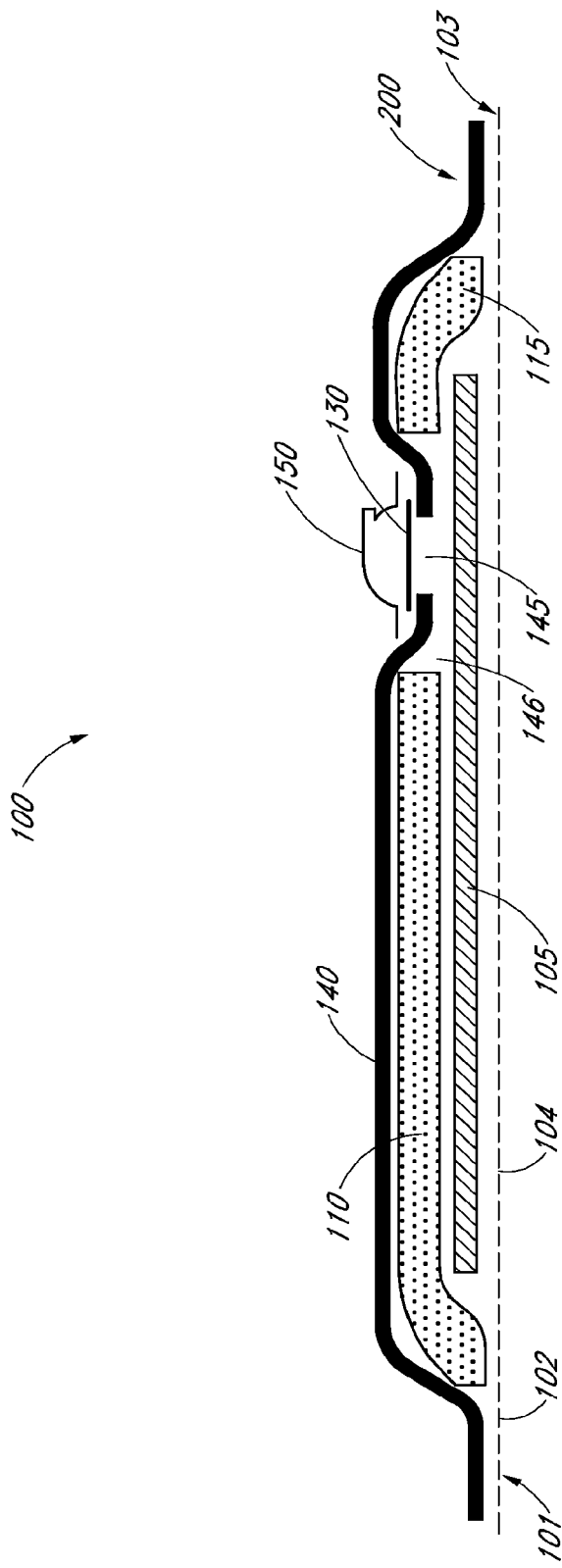
FIG. 1A illustrates a wound dressing.
Figure 1B:
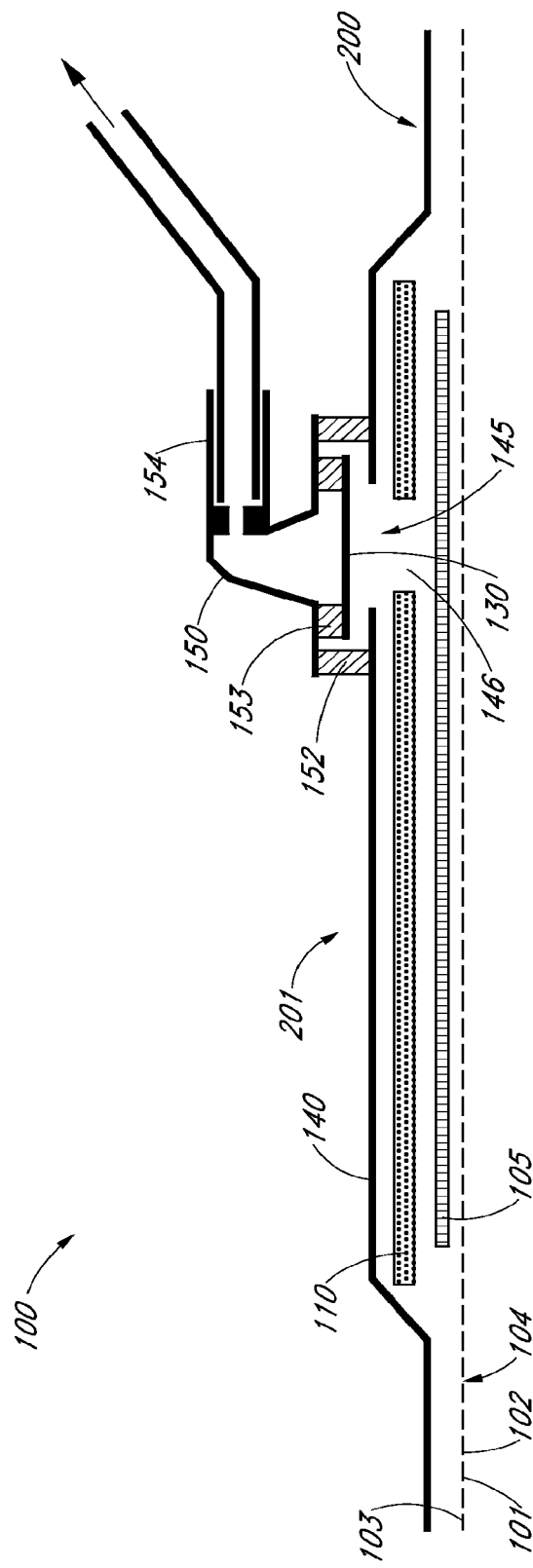
FIG. 1B illustrates another embodiment of a wound dressing.
Figure 2:
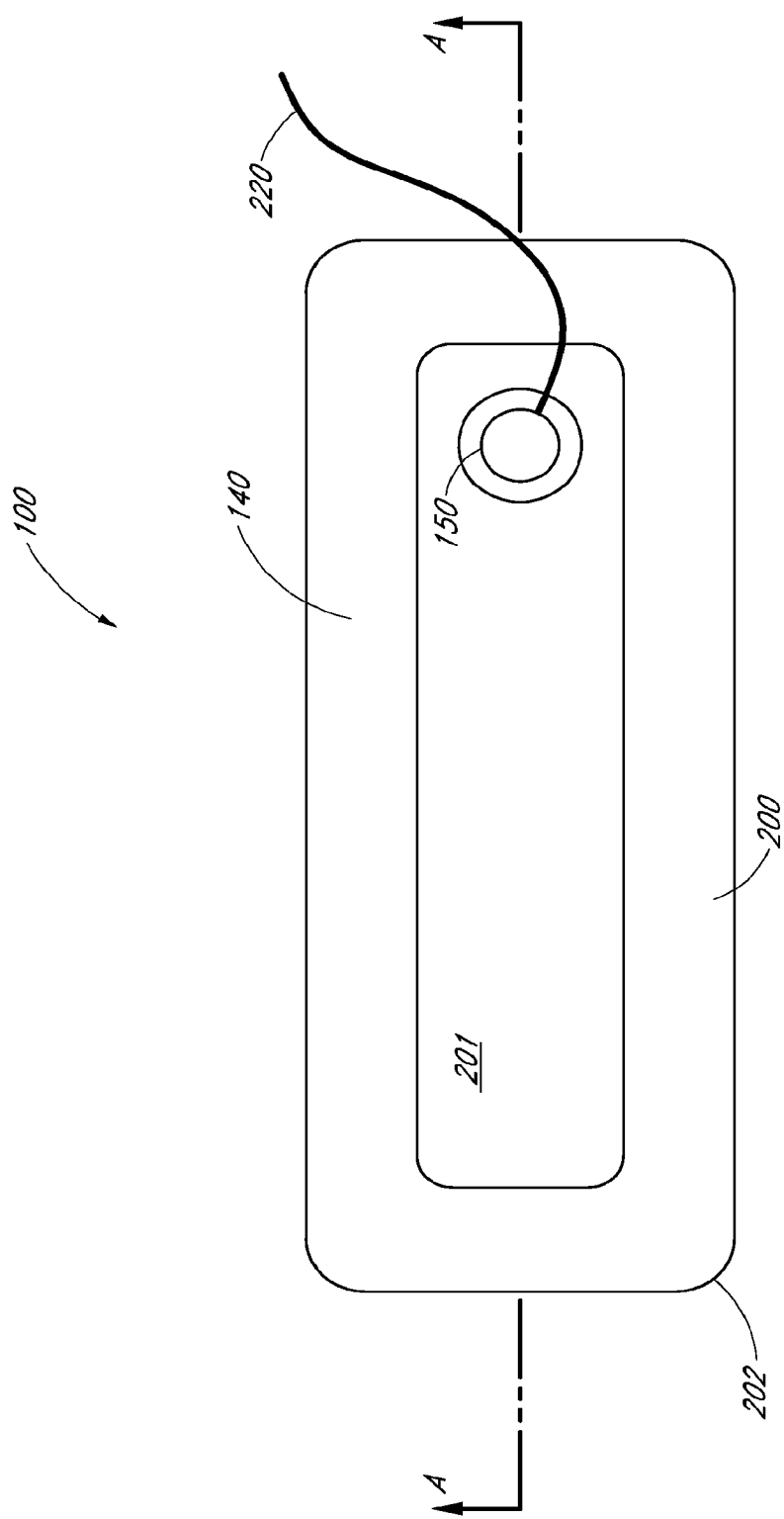
FIG. 2 illustrates a top view of a wound dressing.

FIGS. 1A-B illustrate cross sections through a wound dressing 100 according to an embodiment of the invention. A plan view from above the wound dressing 100 is illustrated in FIG. 2 with the line A-A indicating the location of the cross section shown in FIGS. 1A and 1B. It will be understood that FIGS. 1A-B illustrate a generalized schematic view of an apparatus 100. It will be understood that embodiments of the present invention are generally applicable to use in TNP therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

The wound dressing 100 can be located over a wound site to be treated. The dressing 100 forms a sealed cavity over the wound site. It will be appreciated that throughout this specification reference is made to a wound. In this sense it is to be understood that the term wound is to be broadly construed and encompasses open and closed wounds in which skin is torn, cut or punctured or where trauma causes a contusion. A wound is thus broadly defined as any damaged region of tissue where fluid may or may not be produced. Examples of such wounds include, but are not limited to, incisions, lacerations, abrasions, contusions, burns, diabetic ulcers, pressure ulcers, stoma, surgical wounds, trauma and venous ulcers or the like.

In some embodiments, it may be preferable for the wound site to be filled partially or completely with a wound packing material. This wound packing material is optional, but may be desirable in certain wounds, for example deeper wounds. The wound packing material can be used in addition to the wound dressing 100. The wound packing material generally may comprise a porous and conformable material, for example foam (including reticulated foams), and gauze. Preferably, the wound packing material is sized or shaped to fit within the wound site so as to fill any empty spaces. The wound dressing 100 may then be placed over the wound site and wound packing material overlying the wound site. When a wound packing material is used, once the wound dressing 100 is sealed over the wound site, TNP is transmitted from a pump through the wound dressing 100, through the wound packing material, and to the wound site. This negative pressure draws wound exudate and other fluids or secretions away from the wound site.

It is envisaged that the negative pressure range for the apparatus embodying the present invention may be between about −20 mmHg and −200 mmHg (note that these pressures are relative to normal ambient atmospheric pressure thus, −200 mmHg would be about 560 mmHg in practical terms). In one embodiment, the pressure range may be between about −40 mmHg and −150 mmHg. Alternatively a pressure range of up to −75 mmHg, up to −80 mmHg or over −80 mmHg can be used. Also in other embodiments a pressure range of below −75 mmHg could be used. Alternatively a pressure range of over −100 mmHg could be used or over −150 mmHg.

It will be appreciated that according to certain embodiments of the present invention the pressure provided may be modulated over a period of time according to one or more desired and predefined pressure profiles. For example such a profile may include modulating the negative pressure between two predetermined negative pressures P1 and P2 such that pressure is held substantially constant at P1 for a pre-determined time period T1 and then adjusted by suitable means such as varying pump work or restricting fluid flow or the like, to a new predetermined pressure P2 where the pressure may be held substantially constant for a further predetermined time period T2. Two, three or four or more predetermined pressure values and respective time periods may be optionally utilized. Other embodiments may employ more complex amplitude/frequency wave forms of pressure flow profiles may also be provided e.g. sinusoidal, sore tooth, systolic-diastolic or the like.

As illustrated in FIGS. 1A-B a lower surface 101 of the wound dressing 100 is provided by an optional wound contact layer 102. The wound contact layer 102 can be a polyurethane layer or polyethylene layer or other flexible layer which is perforated, for example via a hot pin process, laser ablation process, ultrasound process or in some other way or otherwise made permeable to liquid and gas. The wound contact layer has a lower surface 101 and an upper surface 103. The perforations 104 are through holes in the wound contact layer which enables fluid to flow through the layer. The wound contact layer helps prevent tissue ingrowth into the other material of the wound dressing. The perforations are small enough to meet this requirement but still allow fluid through. For example, perforations formed as slits or holes having a size ranging from 0.025 mm to 1.2 mm are considered small enough to help prevent tissue ingrowth into the wound dressing while allowing wound exudate to flow into the dressing. The wound contact layer helps hold the whole wound dressing together and helps to create an air tight seal around the absorbent pad in order to maintain negative pressure at the wound. The wound contact layer also acts as a carrier for an optional lower and upper adhesive layer (not shown). For example, a lower pressure sensitive adhesive may be provided on the underside surface 101 of the wound dressing whilst an upper pressure sensitive adhesive layer may be provided on the upper surface 103 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized this helps adhere the wound dressing to the skin around a wound site.

A layer 105 of porous material is located above the wound contact layer. This porous layer, or transmission layer, 105 allows transmission of fluid including liquid and gas away from a wound site into upper layers of the wound dressing. In particular, the transmission layer 105 ensures that an open air channel can be maintained to communicate negative pressure over the wound area even when the absorbent layer has absorbed substantial amounts of exudates. The layer should remain open under the typical pressures that will be applied during negative pressure wound therapy as described above, so that the whole wound site sees an equalized negative pressure. The layer 105 is formed of a material having a three dimensional structure. For example, a knitted or woven spacer fabric (for example Baltex 7970 weft knitted polyester) or a non-woven fabric could be used. Other materials could of course be utilized, and examples of such materials are described below with respect to FIGS. 23-27.

In some embodiments, the transmission layer comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 100 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized.

The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer helps lock the liquid away or itself wicks the liquid onwards towards the cover layer where it can be transpired.

Preferably, to improve the liquid flow across the transmission layer (that is to say perpendicular to the channel region formed between the top and bottom spacer layers, the 3D fabric is treated with a dry cleaning agent (such as, but not limited to, Perchloro Ethylene) to help remove any manufacturing products such as mineral oils, fats and/or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

A layer 110 of absorbent material is provided above the transmission layer 105. The absorbent material which may be a foam or non-woven natural or synthetic material and which may optionally include or be super-absorbent material forms a reservoir for fluid, particularly liquid, removed from the wound site and draws those fluids towards a cover layer 140. The material of the absorbent layer also prevents liquid collected in the wound dressing from flowing in a sloshing manner. The absorbent layer 110 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 110 may typically be manufactured from ALLEVYN™ foam, Freudenberg 114-224-4 and/or Chem-Posite™11C-450.

In some embodiments, the absorbent layer is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. Also, all regions of the absorbent layer are provided with liquid.

The wicking action also assists in bringing liquid into contact with the upper cover layer to aid increase transpiration rates of the dressing.

The wicking action also assists in delivering liquid downwards towards the wound bed when exudation slows or halts. This delivery process helps maintain the transmission layer and lower wound bed region in a moist state which helps prevent crusting within the dressing (which could lead to blockage) and helps maintain an environment optimized for wound healing.

In some embodiments, the absorbent layer may be an air-laid material. Heat fusible fibers may optionally be used to assist in holding the structure of the pad together. It will be appreciated that rather than using super-absorbing particles or in addition to such use, super-absorbing fibers may be utilized according to certain embodiments of the present invention. An example of a suitable material is the Product Chem-Posite™ 11 C available from Emerging Technologies Inc (ETi) in the USA.

Optionally, according to certain embodiments of the present invention, the absorbent layer may include synthetic stable fibers and/or bi-component stable fibers and/or natural stable fibers and/or super-absorbent fibers. Fibers in the absorbent layer may be secured together by latex bonding or thermal bonding or hydrogen bonding or a combination of any bonding technique or other securing mechanism. In some embodiments, the absorbent layer is formed by fibers which operate to lock super-absorbent particles within the absorbent layer. This helps ensure that super-absorbent particles do not move external to the absorbent layer and towards an underlying wound bed. This is particularly helpful because when negative pressure is applied there is a tendency for the absorbent pad to collapse downwards and this action would push super-absorbent particle matter into a direction towards the wound bed if they were not locked away by the fibrous structure of the absorbent layer.

The absorbent layer may comprise a layer of multiple fibers. Preferably, the fibers are strand-like and made from cellulose, polyester, viscose or the like. Preferably, dry absorbent particles are distributed throughout the absorbent layer ready for use. In some embodiments, the absorbent layer comprises a pad of cellulose fibers and a plurality of super absorbent particles. In additional embodiments, the absorbent layer is a non-woven layer of randomly orientated cellulose fibers.

Super-absorber particles/fibers may be, for example, sodium polyacrylate or carbomethoxycellulose materials or the like or any material capable of absorbing many times its own weight in liquid. In some embodiments, the material can absorb more than five times its own weight of 0.9% W/W saline, etc. In some embodiments, the material can absorb more than 15 times its own weight of 0.9% W/W saline, etc. In some embodiments, the material is capable of absorbing more than 20 times its own weight of 0.9% W/W saline, etc. Preferably, the material is capable of absorbing more than 30 times its own weight of 0.9% W/W saline, etc.

Preferably, the particles of superabsorber are very hydrophilic and grab the fluid as it enters the dressing, swelling up on contact. An equilibrium is set up within the dressing core whereby moisture passes from the superabsorber into the dryer surrounding area and as it hits the top film the film switches and the fluid vapor starts to be transpired. A moisture gradient is established within the dressing to continually remove fluid from the wound bed and ensure the dressing does not become heavy with exudate.

Preferably the absorbent layer includes at least one through hole located so as to underly the suction port. As illustrated in FIGS. 1A-B a single through hole can be used to produce an opening underlying the port 150. It will be appreciated that multiple openings could alternatively be utilized. Additionally should more than one port be utilized according to certain embodiments of the present invention one or multiple openings may be made in the super-absorbent layer in registration with each respective port. Although not essential to certain embodiments of the present invention the use of through holes in the super-absorbent layer provide a fluid flow pathway which is particularly unhindered and this is useful in certain circumstances.

Where an opening is provided in the absorbent layer the thickness of the layer itself will act as a stand-off separating any overlying layer from the upper surface (that is to say the surface facing away from a wound in use) of the transmission layer 105. An advantage of this is that the filter of the port is thus decoupled from the material of the transmission layer. This helps reduce the likelihood that the filter will be wetted out and thus will occlude and block further operation.

Use of one or more through holes in the absorption layer also has the advantage that during use if the absorbent layer contains a gel forming material, such as superabsorber, that material as it expands to absorb liquid, does not form a barrier through which further liquid movement and fluid movement in general cannot pass. In this way each opening in the absorbent layer provides a fluid pathway between the transmission layer directly to the wound facing surface of the filter and then onwards into the interior of the port.

A gas impermeable, but moisture vapor permeable, cover layer 140 extends across the width of the wound dressing. The cover layer, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer and a wound site where a negative pressure can be established. The cover layer 140 is sealed to the wound contact layer 102 in a border region 200 around the circumference of the dressing, ensuring that no air is drawn in through the border area, for example via adhesive or welding techniques. The cover layer 140 protects the wound from external bacterial contamination (bacterial barrier) and allows liquid from wound exudates to be transferred through the layer and evaporated from the film outer surface. The cover layer 140 typically comprises two layers; a polyurethane film and an adhesive pattern spread onto the film. The polyurethane film is moisture vapor permeable and may be manufactured from a material that has an increased water transmission rate when wet.

The absorbent layer 110 may be of a greater area than the transmission layer 105, such that the absorbent layer overlaps the edges of the transmission layer 105, thereby ensuring that the transmission layer does not contact the cover layer 140. This provides an outer channel 115 of the absorbent layer 110 that is in direct contact with the wound contact layer 102, which aids more rapid absorption of exudates to the absorbent layer. Furthermore, this outer channel 115 ensures that no liquid is able to pool around the circumference of the wound cavity, which may otherwise seep through the seal around the perimeter of the dressing leading to the formation of leaks.

In order to ensure that the air channel remains open when a vacuum is applied to the wound cavity, the transmission layer 105 must be sufficiently strong and non-compliant to resist the force due to the pressure differential. However, if this layer comes into contact with the relatively delicate cover layer 140, it can cause the formation of pin-hole openings in the cover layer 140 which allow air to leak into the wound cavity. This may be a particular problem when a switchable type polyurethane film is used that becomes weaker when wet. The absorbent layer 110 is generally formed of a relatively soft, non-abrasive material compared to the material of the transmission layer 105 and therefore does not cause the formation of pin-hole openings in the cover layer. Thus by providing an absorbent layer 110 that is of greater area than the transmission layer 105 and that overlaps the edges of the transmission layer 105, contact between the transmission layer and the cover layer is prevented, avoiding the formation of pin-hole openings in the cover layer 140.

The absorbent layer 110 is positioned in fluid contact with the cover layer 140. As the absorbent layer absorbs wound exudate, the exudate is drawn towards the cover layer 140, bringing the water component of the exudate into contact with the moisture vapor permeable cover layer. This water component is drawn into the cover layer itself and then evaporates from the top surface of the dressing. In this way, the water content of the wound exudate can be transpired from the dressing, reducing the volume of the remaining wound exudate that is to be absorbed by the absorbent layer 110, and increasing the time before the dressing becomes full and must be changed. This process of transpiration occurs even when negative pressure has been applied to the wound cavity, and it has been found that the pressure difference across the cover layer when a negative pressure is applied to the wound cavity has negligible impact on the moisture vapor transmission rate across the cover layer.

An orifice 145 is provided in the cover film 140 to allow a negative pressure to be applied to the dressing 100. A suction port 150 is sealed to the top of the cover film 140 over the orifice 145, and communicates negative pressure through the orifice 145. A length of tubing 220 may be coupled at a first end to the suction port 150 and at a second end to a pump unit (not shown) to allow fluids to be pumped out of the dressing. The port may be adhered and sealed to the cover film 140 using an adhesive such as an acrylic, cyanoacrylate, epoxy, UV curable or hot melt adhesive. The port 150 is formed from a soft polymer, for example a polyethylene, a polyvinyl chloride, a silicone or polyurethane having a hardness of 30 to 90 on the Shore A scale.

An aperture or through-hole 146 is provided in the absorbent layer 110 beneath the orifice 145 such that the orifice is connected directly to the transmission layer 105. This allows the negative pressure applied to the port 150 to be communicated to the transmission layer 105 without passing through the absorbent layer 110. This ensures that the negative pressure applied to the wound site is not inhibited by the absorbent layer as it absorbs wound exudates. In other embodiments, no aperture may be provided in the absorbent layer 110, or alternatively a plurality of apertures underlying the orifice 145 may be provided.

As shown in FIG. 1A, one embodiment of the wound dressing 100 comprises an aperture 146 in the absorbent layer 100 situated underneath the port 150. In use, for example when negative pressure is applied to the dressing 100, a wound facing portion of the port 150 may thus come into contact with the transmission layer 105, which can thus aid in transmitting negative pressure to the wound site even when the absorbent layer 110 is filled with wound fluids. Some embodiments may have the cover layer 140 be at least partly adhered to the transmission layer 105. In some embodiments, the aperture 146 is at least 1-2 mm larger than the diameter of the wound facing portion of the port 150, or the orifice 145.

A filter element 130 that is impermeable to liquids, but permeable to gases is provided to act as a liquid barrier, and to ensure that no liquids are able to escape from the wound dressing. The filter element may also function as a bacterial barrier. Typically the pore size is 0.2 µm. Suitable materials for the filter material of the filter element 130 include 0.2 micron Gore™ expanded PTFE from the MMT range, PALL Versapore™ 200R, and Donaldson™ TX6628. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter. The filter element can be attached or sealed to the port and/or the cover film 140 over the orifice 145. For example, the filter element 130 may be molded into the port 150, or may be adhered to both the top of the cover layer 140 and bottom of the port 150 using an adhesive such as, but not limited to, a UV cured adhesive.

It will be understood that other types of material could be used for the filter element 130. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. In some embodiments of the invention, filter element 130 comprises a support layer and an acrylic co-polymer membrane formed on the support layer. Preferably the wound dressing 100 according to certain embodiments of the present invention uses microporous hydrophobic membranes (MHMs). Numerous polymers may be employed to form MHMs. For example, PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter element 130 may also include an odor absorbent material, for example activated charcoal, carbon fiber cloth or Vitec Carbotec-RT Q2003073 foam, or the like. For example, an odor absorbent material may form a layer of the filter element 130 or may be sandwiched between microporous hydrophobic membranes within the filter element.

The filter element 130 thus enables gas to be exhausted through the orifice 145. Liquid, particulates and pathogens however are contained in the dressing.

In FIG. 1B, an embodiment of the wound dressing 100 is illustrated which comprises spacer elements 152, 153 in conjunction with the port 150 and the filter 130. With the addition of such spacer elements 152, 153, the port 150 and filter 130 may be supported out of direct contact with the absorbent layer 110 and/or the transmission layer 105. The absorbent layer 110 may also act as an additional spacer element to keep the filter 130 from contacting the transmission layer 105. Accordingly, with such a configuration contact of the filter 130 with the transmission layer 105 and wound fluids during use may thus be minimized. As contrasted with the embodiment illustrated in FIG. 1A, the aperture 146 through the absorbent layer 110 may not necessarily need to be as large or larger than the port 150, and would thus only need to be large enough such that an air path can be maintained from the port to the transmission layer 105 when the absorbent layer 110 is saturated with wound fluids.

In particular for embodiments with a single port 150 and through hole, it may be preferable for the port 150 and through hole to be located in an off-center position as illustrated in FIGS. 1A-B and in FIG. 2. Such a location may permit the dressing 100 to be positioned onto a patient such that the port 150 is raised in relation to the remainder of the dressing 100. So positioned, the port 150 and the filter 130 may be less likely to come into contact with wound fluids that could prematurely occlude the filter 130 so as to impair the transmission of negative pressure to the wound site.

FIG. 11 shows a plan view of a suction port 150 according to some embodiments of the invention. The suction port comprises a sealing surface 152 for sealing the port to a wound dressing, a connector portion 154 for connecting the suction port 150 to a source of negative pressure, and a hemispherical body portion 156 disposed between the sealing surface 152 and the connector portion 154. Sealing surface 152 comprises a flange that provides a substantially flat area to provide a good seal when the port 150 is sealed to the cover layer 140. Connector portion 154 is arranged to be coupled to the external source of negative pressure via a length of tube 220.

According to some embodiments, the filter element 130 forms part of the bacterial barrier over the wound site, and therefore it is important that a good seal is formed and maintained around the filter element. However, it has been determined that a seal formed by adhering the filter element 130 to the cover layer 140 is not sufficiently reliable. This is a particular problem when a moisture vapor permeable cover layer is used, as the water vapor transpiring from the cover layer 140 can affect the adhesive, leading to breach of the seal between the filter element and the cover layer. Thus, according to some embodiments of the invention an alternative arrangement for sealing the filter element 130 to stop liquid from entering the connector portion 154 is employed.

FIG. 12 illustrates a cross section through the suction port 150 of FIG. 11 according to some embodiments of the invention, the line A-A in FIG. 11 indicating the location of the cross section. In the suction port of FIG. 12, the suction port 150 further comprises filter element 130 arranged within the body portion 156 of the suction port 150. A seal between the suction port 150 and the filter element 130 is achieved by molding the filter element within the body portion of the suction port 150.

FIG. 13 illustrates a cross section through the suction port 150 of FIG. 11 according to some embodiments of the invention. In the suction port of FIG. 13, the filter element 130 is sealed to the sealing surface 152 of the suction port 150. The filter element may be sealed to the sealing surface using an adhesive or by welding the filter element to the sealing surface.

By providing the filter element 130 as part of the suction port 150, as illustrated in FIGS. 12 and 13, the problems associated with adhering the filter element to the cover layer 140 are avoided allowing a reliable seal to be provided. Furthermore, providing a sub-assembly having the filter element 130 included as part of the suction port 150 allows for simpler and more efficient manufacture of the wound dressing 100.

While the suction port 150 has been described in the context of the wound dressing 100 of FIG. 1, it will be understood that the embodiments of FIGS. 12 and 13 are applicable to any wound dressing for applying a negative pressure to a wound, wherein wound exudate drawn from the wound is retained within the dressing. According to some embodiments of the invention, the suction port 150 may be manufactured from a transparent material in order to allow a visual check to be made by a user for the ingress of wound exudate into the suction port 150.

The wound dressing 100 and its methods of manufacture and use as described herein may also incorporate features, configurations and materials described in the following patents and patent applications incorporated by reference in their entireties: U.S. Pat. Nos. 7,524,315, 7,708,724, and 7,909,805; U.S. Patent Application Publication Nos. 2005/0261642, 2007/0167926, 2009/0012483, 2009/0254054, 2010/0160879, 2010/0160880, 2010/0174251, 2010/0274207, 2010/0298793, 2011/0009838, 2011/0028918, 2011/0054421, and 2011/0054423; as well as U.S. application Ser. No. 12/941,390, filed Nov. 8, 2010, Ser. No. 29/389,782, filed Apr. 15, 2011, and Ser. No. 29/389,783, filed Apr. 15, 2011. From these incorporated by reference patents and patent applications, features, configurations, materials and methods of manufacture or use for similar components to those described in the present disclosure may be substituted, added or implemented into embodiments of the present application.

In operation the wound dressing 100 is sealed over a wound site forming a wound cavity. A pump unit (illustrated in FIG. 28 and described in further detail below) applies a negative pressure at a connection portion 154 of the port 150 which is communicated through the orifice 145 to the transmission layer 105. Fluid is drawn towards the orifice through the wound dressing from a wound site below the wound contact layer 102. The fluid moves towards the orifice through the transmission layer 105. As the fluid is drawn through the transmission layer 105 wound exudate is absorbed into the absorbent layer 110.

Turning to FIG. 2 which illustrates a wound dressing 100 in accordance with an embodiment of the present invention one can see the upper surface of the cover layer 140 which extends outwardly away from a centre of the dressing into a border region 200 surrounding a central raised region 201 overlying the transmission layer 105 and the absorbent layer 110. As indicated in FIG. 2 the general shape of the wound dressing is rectangular with rounded corner regions 202. It will be appreciated that wound dressings according to other embodiments of the present invention can be shaped differently such as square, circular or elliptical dressings, or the like.

The wound dressing 100 may be sized as necessary for the size and type of wound it will be used in. In some embodiments, the wound dressing 100 may measure between 20 and 40 cm on its long axis, and between 10 to 25 cm on its short axis. For example, dressings may be provided in sizes of 10×20 cm, 10×30 cm, 10×40 cm, 15×20 cm, and 15×30 cm. In some embodiments, the wound dressing 100 may be a square-shaped dressing with sides measuring between 15 and 25 cm (e.g., 15×15 cm, 20×20 cm and 25×25 cm). The absorbent layer 110 may have a smaller area than the overall dressing, and in some embodiments may have a length and width that are both about 3 to 10 cm shorter, more preferably about 5 cm shorter, than that of the overall dressing 100. In some rectangular-shape embodiments, the absorbent layer 110 may measure between 10 and 35 cm on its long axis, and between 5 and 10 cm on its short axis. For example, absorbent layers may be provided in sizes of 5.6×15 cm or 5×10 cm (for 10×20 cm dressings), 5.6×25 cm or 5×20 cm (for 10×30 cm dressings), 5.6×35 cm or 5×30 cm (for 10×40 cm dressings), 10×15 cm (for 15×20 cm dressings), and 10×25 cm (for 15×30 cm dressings). In some square-shape embodiments, the absorbent layer 110 may have sides that are between 10 and 20 cm in length (e.g., 10×10 cm for a 15×15 cm dressing, 15×15 cm for a 20×20 cm dressing, or 20×20 cm for a 25×25 cm dressing). The transmission layer 105 is preferably smaller than the absorbent layer, and in some embodiments may have a length and width that are both about 0.5 to 2 cm shorter, more preferably about 1 cm shorter, than that of the absorbent layer. In some rectangular-shape embodiments, the transmission layer may measure between 9 and 34 cm on its long axis and between 3 and 5 cm on its short axis. For example, transmission layers may be provided in sizes of 4.6×14 cm or 4×9 cm (for 10×20 cm dressings), 4.6×24 cm or 4×19 cm (for 10×30 cm dressings), 4.6×34 cm or 4×29 cm (for 10×40 cm dressings), 9×14 cm (for 15×20 cm dressings), and 9×24 cm (for 15×30 cm dressings). In some square-shape embodiments, the transmission layer may have sides that are between 9 and 19 cm in length (e.g., 9×9 cm for a 15×15 cm dressing, 14×14 cm for a 20×20 cm dressing, or 19×19 cm for a 25×25 cm dressing).

It will be understood that according to embodiments of the present invention the wound contact layer is optional. This layer is, if used, porous to water and faces an underlying wound site. A transmission layer 105 such as an open celled foam, or a knitted or woven spacer fabric is used to distribute gas and fluid removal such that all areas of a wound are subjected to equal pressure. The cover layer together with the filter layer forms a substantially liquid tight seal over the wound. Thus when a negative pressure is applied to the port 150 the negative pressure is communicated to the wound cavity below the cover layer. This negative pressure is thus experienced at the target wound site. Fluid including air and wound exudate is drawn through the wound contact layer and transmission layer 105. The wound exudate drawn through the lower layers of the wound dressing is dissipated and absorbed into the absorbent layer 110 where it is collected and stored. Air and moisture vapor is drawn upwards through the wound dressing through the filter layer and out of the dressing through the suction port. A portion of the water content of the wound exudate is drawn through the absorbent layer and into the cover layer 140 and then evaporates from the surface of the dressing.

As discussed above, when a negative pressure is applied to a wound dressing sealed over a wound site, fluids including wound exudate are drawn from the wound site and through the transmission layer 105 towards the orifice 145. Wound exudate is then drawn into the absorbent layer 110 where it is absorbed. However, some wound exudate may not be absorbed and may move to the orifice 145. Filter element 130 provides a barrier that stops any liquid in the wound exudate from entering the connection portion 154 of the suction port 150. Therefore, unabsorbed wound exudate may collect underneath the filter element 130. If sufficient wound exudate collects at the filter element, a layer of liquid will form across the surface of filter element 130 and the filter element will become blocked as the liquid cannot pass through the filter element 130 and gases will be stopped from reaching the filter element by the liquid layer. Once the filter element becomes blocked, negative pressure can no longer be communicated to the wound site, and the wound dressing must be changed for a fresh dressing, even though the total capacity of the absorbent layer has not been reached.

In a preferred embodiment, the port 150, along with any aperture 146 in the absorbing layer 110 situated below it, generally aligns with the mid-longitudinal axis A-A illustrated in FIG. 2. Preferably, the port 150 and any such aperture 146 are situated closer to one end of the dressing, contrasted with a central position. In some embodiments, the port may be located at a corner of the dressing 100. For example, in some rectangular embodiments, the port 150 may be located between 4 and 6 cm from the edge of the dressing, with the aperture 146 located 2 to 3 cm from the edge of the absorbent layer. In some square embodiments, the port 150 may be located between 5 to 8 cm from the corner of the dressing, with the aperture 146 located 3 to 5 cm from the corner of the absorbent layer.

Certain orientations of the wound dressing may increase the likelihood of the filter element 130 becoming blocked in this way, as the movement of the wound exudate through the transmission layer may be aided by the effect of gravity. Thus, if due to the orientation of the wound site and wound dressing, gravity acts to increase the rate at which wound exudate is drawn towards the orifice 145, the filter may become blocked with wound exudate more quickly. Thus, the wound dressing would have to be changed more frequently and before the absorbent capacity of the absorbent layer 110 has been reached.

In order to avoid the premature blocking of the wound dressing 100 by wound exudate drawn towards the orifice 145 some embodiments of the invention include at least one element configured to reduce the rate at which wound exudate moves towards the orifice 145. The at least one element may increase the amount of exudate that is absorbed into the absorbent layer before reaching the orifice 145 and/or may force the wound exudate to follow a longer path through the dressing before reaching the orifice 145, thereby increasing the time before the wound dressing becomes blocked.

Figure 3:
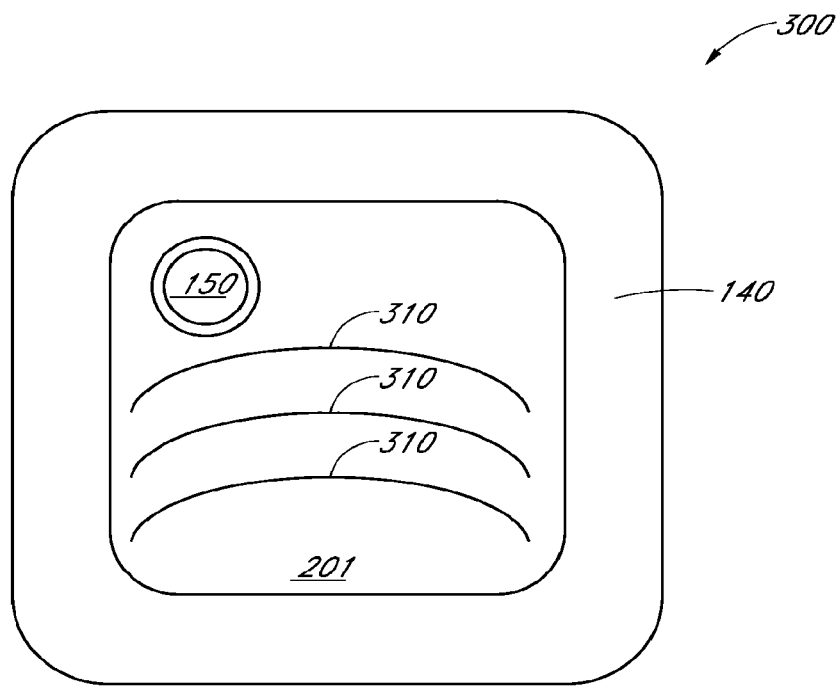
FIG. 3 illustrates a top view of a wound dressing including baffle elements.

FIG. 3 shows a plan view of a wound dressing including baffle elements that reduce the rate at which wound exudate moves towards the orifice according to one embodiment of the invention. The wound dressing illustrated in FIG. 3 is similar to that shown in FIGS. 1 and 2, but includes a number of baffle elements 310 disposed across the central raised region 201. The baffle elements 310 form barriers in the central region of the dressing, which arrest the movement of wound exudate towards the orifice.

Embodiments of baffle elements that may be used in the wound dressing described herein are preferably at least partly flexible, so as to permit the wound dressing to flex and conform with the skin of the patient surrounding the wound site. When so present in the wound dressing, the baffle elements are preferably constructed so as to at least partially prevent liquid from flowing directly to the wound dressing port or orifice and its associated filter, if so provided. The baffle elements thus increase the distance that liquids may require to reach the port, which may help in absorbing these fluids into the absorbent or superabsorbent material of the wound dressing.

According to some embodiments of the invention, the baffle element may comprise a sealing region in which the absorbent layer 110 and transmission layer 105 are absent and cover layer 140 is sealed to the wound contact layer 101. Thus, the baffle element presents a barrier to the motion of the wound exudate, which must therefore follow a path that avoids the baffle element. Thus the time taken for the wound exudate to reach the orifice is increased.

In some embodiments, the baffle elements may be an insert of a substantially non-porous material, for example a closed-cell polyethylene foam, placed inside the dressing. In some cases, it may be preferable to place such an inserted baffle element in a sealing region where one or more of the absorbent layer 110 and/or transmission layer 105 are absent. A sealant, for example a viscous curing sealant such as a silicone sealant, could be placed or injected as a thin strip so as to form a baffle element that is substantially liquid impermeable. Such a baffle element could be placed or injected into a region of the transmission layer 105 and/or absorbent layer 110, or also a sealing region where the absorbent layer 110 and/or transmission layer 105 are absent.

Figure 6:
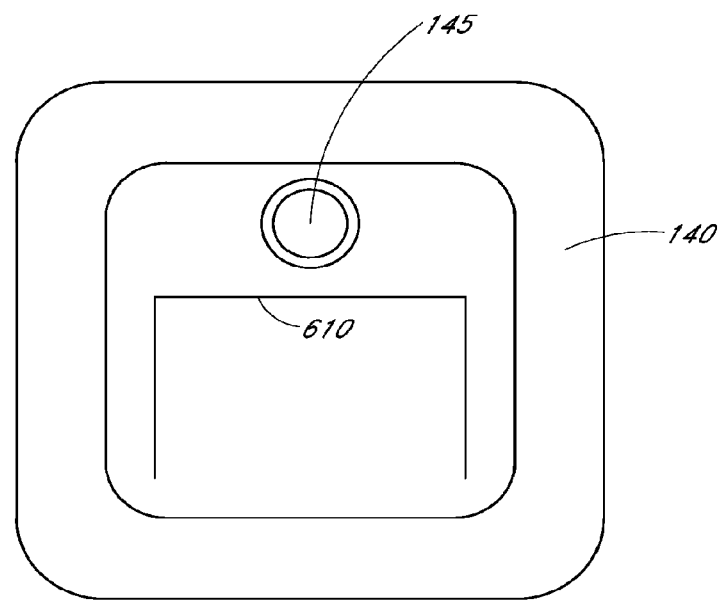
FIG. 6 illustrates a top view of a wound dressing including a single baffle element.

FIG. 6 illustrates a wound dressing including a baffle element according to a further embodiment of the invention. A single baffle element 610 provides a cup shaped barrier between the bulk of the absorbent layer 110 and the orifice 145. Thus wound exudate that is initially drawn from the wound site within the region defined by the baffle element 610, must follow a path around the outside of the cup shaped barrier to reach the orifice 145. As will be recognized, the baffle element 610 reduces the effect of gravity on reducing the time taken for the wound exudate to move to the orifice 145, as for most orientations of the wound dressing at least a part of the path taken by the wound exudate will be against the force of gravity.

The embodiments of FIGS. 3 and 6 have been described with respect to a wound dressing having a structure as shown in FIG. 1. However, it will be understood that the baffle elements could equally be applied to a wound dressing in which the transmission layer 105 was absent.

Figure 4:
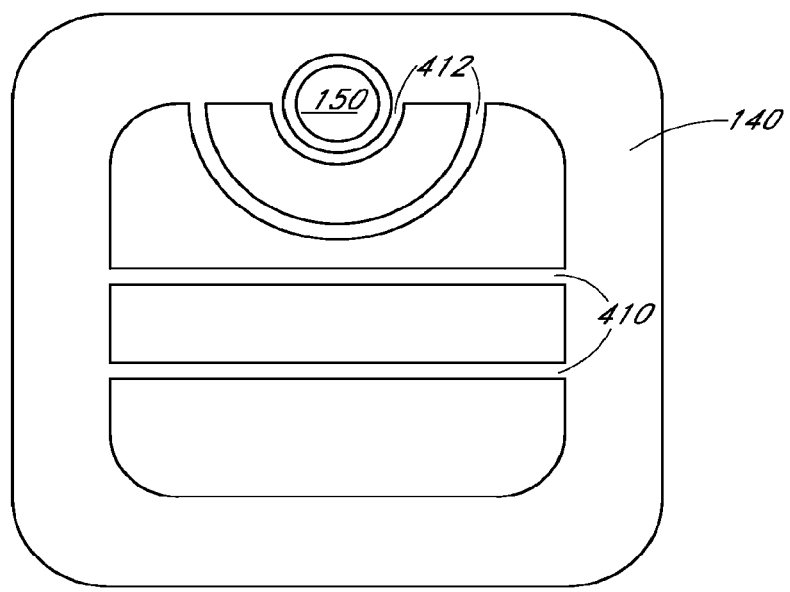
FIG. 4 illustrates a top view of a further wound dressing including baffle elements.

FIG. 4 shows a plan view of a wound dressing including the at least one element according to one embodiment of the invention in which a number of baffle elements 410 are provided that extend across the width of the central region 201 of the wound dressing, with further baffle elements 412 formed in a semi-circular path around the orifice 145.

Figure 5:
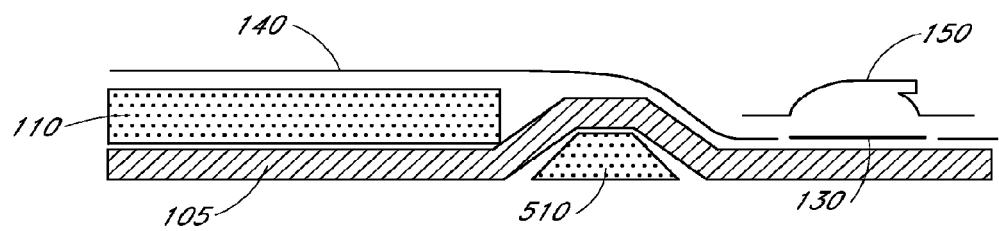
FIG. 5 illustrates a baffle element according to one embodiment.

FIG. 5 illustrates the configuration of baffle elements 410 according to some embodiments of the invention. The baffle element comprises a channel of absorbent material 510 underlying the transmission layer 105. A channel in the absorbent layer 110 is located over the baffle element 410 so that the transmission layer is in contact with the cover layer 140 in the region of the baffle element 410. Thus, wound exudate that is moving along a lower surface of the transmission layer 105, and has therefore not been drawn into absorbent layer 110, will come into contact with and be absorbed by the channel of absorbent material 510.

Alternatively, or additionally, baffle elements may comprise one or more channels provided in the surface of the transmission layer 105 underlying and abutting the absorbent layer 110. In use, when negative pressure is applied to the wound dressing, the absorbent layer 110 will be drawn into the channel. The channel in the transmission layer may have a depth substantially equal to the depth of the transmission layer, or may have a depth less than the depth of the transmission layer. The dimensions of the channel may be chosen to ensure that the channel is filled by the absorbent layer 110 when negative pressure is applied to the wound dressing. According to some embodiments, the channel in the transmission layer comprises a channel of absorbent material in the transmission layer 105.

Figure 14A:
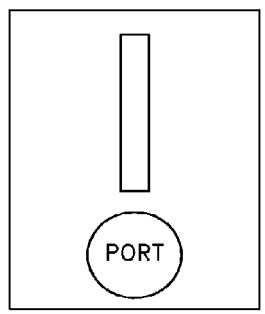
Figure 14B:
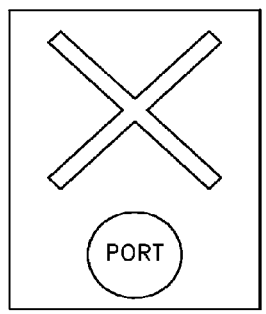
Figure 14C:
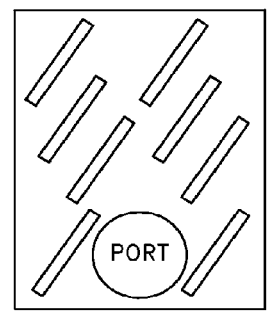
Figure 14D:
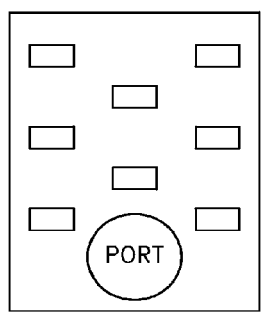
Figure 14E:
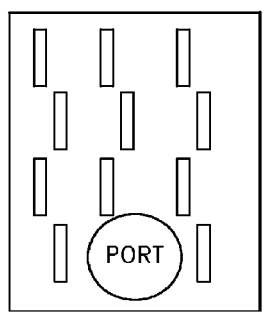

The baffle elements may be formed into a range of shapes and patterns, for example FIGS. 14A to 14L illustrate wound dressings having a number of different exemplifying configurations of baffle elements. FIG. 14A illustrates a linear baffle element in a vertical configuration aligned in the direction of the port or orifice. FIG. 14B illustrates an X-shaped baffle element. FIGS. 14C-E illustrate embodiments of wound dressings with multiple baffle elements, aligned in a generally diagonal, horizontal, or vertical manner.

Figure 14F:
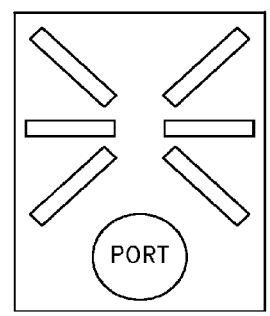

FIG. 14F illustrates baffle elements arranged in a six-armed starburst configuration, with a center portion left open. FIG. 14G illustrates a W-shaped baffle element on the wound dressing in a position distal to the port or orifice. In FIG. 14H, an 3-by-3 array of X-shaped baffle elements is provided on the wound dressing, although it will be understood that more or less X-shaped baffle elements may be used. FIG. 14I shows an embodiment with a plurality of rectangular baffle elements, and wherein one or more baffle elements are located underneath the port in the wound dressing. FIGS. 14J-K illustrate wound dressing embodiments with longer diagonal and horizontal baffle elements. In FIG. 14L, rectangular baffle elements are present on this embodiment of a wound dressing, wherein the baffle elements are of different sizes.

Figure 15:
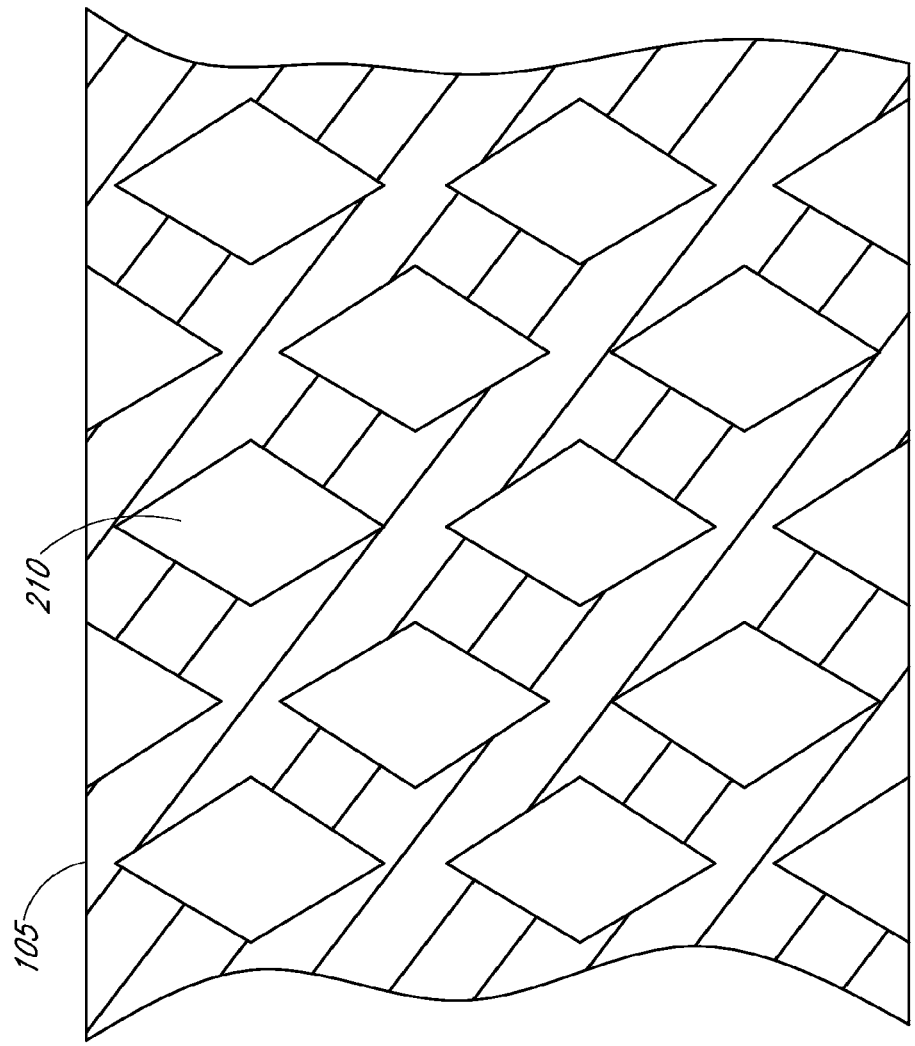
FIG. 15 illustrates an exemplifying configuration of vias in a transmission layer of a wound dressing.

According to some embodiments of the invention, the at least one element comprises an array of vias, or troughs, in the transmission layer 105. FIG. 15 illustrates a transmission layer 105 that is perforated with diamond shaped vias 210. The vias 210 are arranged such that no linear pathway exists through the pattern of vias that does not intersect with one or more of the vias 210.

When negative pressure is applied to the wound dressing, the absorbent layer 110 is drawn into the vias 210, increasing the area of the absorbent layer that comes into contact with wound exudate being drawn through the transmission layer 105. Alternatively, the vias 210 may be filled with further absorbent material for absorbing wound exudate being drawn through the transmission layer 105. The vias may extend through the depth of the transmission layer 105, or may extend through only part of the transmission layer.

Wound exudate moving through the transmission layer 105 under the influence of gravity will fall through the transmission layer in a substantially linear manner. Any such linear pathways will, at some point, intersect with one of the vias 210, and thus the exudate will be brought into contact with absorbent material within the vias 210. Wound exudate coming into contact with absorbent material will be absorbed, stopping the flow of the wound exudate through the transmission layer 105, and reducing the amount of unabsorbed wound exudate that may otherwise pool around the orifice. It will be appreciated that the vias are not limited to diamond shapes, and that any pattern of vias may be used. Preferably, the vias will be arranged to ensure that all linear paths through the transmission layer 105 intersect with at least one via. The pattern of vias may be chosen to minimize the distance that wound exudate is able to travel though the transmission layer before encountering a via and being absorbed.

Figure 7:
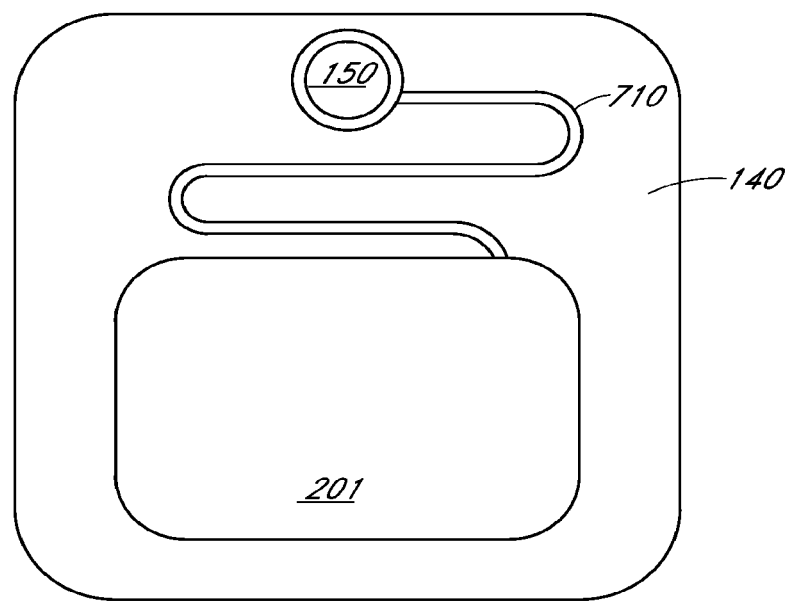
FIG. 7 illustrates a top view of a wound dressing including an air channel.

FIG. 7 illustrates a wound dressing in accordance with some embodiments of the invention in which the at least one element comprises an air channel 710 connecting the central region 201 of the wound dressing to the orifice 145. In the embodiment of FIG. 7, the air channel 710 extends from an edge region of the transmission layer 105 and connects the transmission layer to the orifice 145.

In use, wound exudate is drawn towards the orifice 145 by the application of negative pressure at the suction port 150. However, the air channel 710 present a relatively long serpentine path to be followed by the wound exudate before it reaches the orifice 145. This long path increases the time that negative pressure can be applied to the dressing before wound exudate traverses the distance between the transmission layer and the orifice and blocks the filter element 130, thereby increasing the time the dressing can be in use before it must be replaced.

Figure 8:
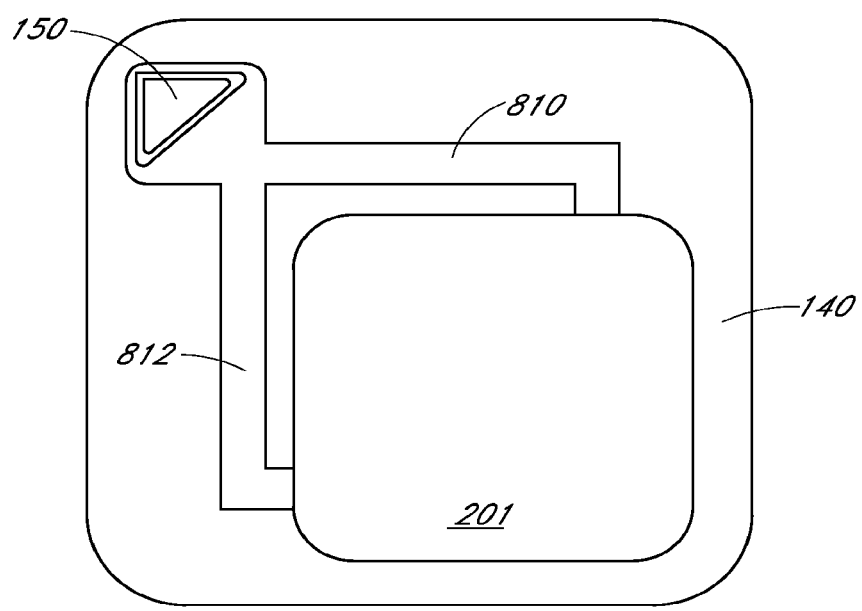
FIG. 8 illustrates a top view of a wound dressing including two air channels.

FIG. 8 illustrates a wound dressing in accordance with one embodiment of the invention in which the at least one element comprises air channels 810 and 812 connecting the central region 201 of the wound dressing to the orifice 145. Channels 810 and 812 are coupled to the transmission layer at substantially opposite corners of the central region 201.

The wound dressing shown in FIG. 8 reduces the effect of gravity on the time taken for the orifice to become blocked. If the wound dressing is in an orientation in which wound exudate moves under the influence of gravity towards the edge region of the transmission layer connected to air channel 810, the effect of gravity will be to move wound exudate away from the edge region of the transmission layer coupled to air channel 812, and vice versa. Thus, the embodiment of FIG. 8 provides alternative air channels for coupling the negative pressure to the transmission layer such that, should one air channel become blocked a remaining air channel should remain open and able to communicate the negative pressure to the transmission layer 105, thereby increasing the time before negative pressure can no longer be applied to the wound dressing and the dressing must be changed.

Further embodiments of the invention may comprise greater numbers of air channels connecting the transmission layer 105 to the orifice.

According to some embodiments of the invention, two or more orifices may be provided in the cover layer 140 for applying the negative pressure to the wound dressing. The two or more orifices can be distributed across the cover layer 140 such that if one orifice becomes blocked by wound exudate due to the wound dressing being in a particular orientation, at least one remaining orifice would be expected to remain unblocked. Each orifice is in fluid communication with a wound chamber defined by the wound dressing, and is therefore able to communicate the negative pressure to the wound site.

Figure 9:
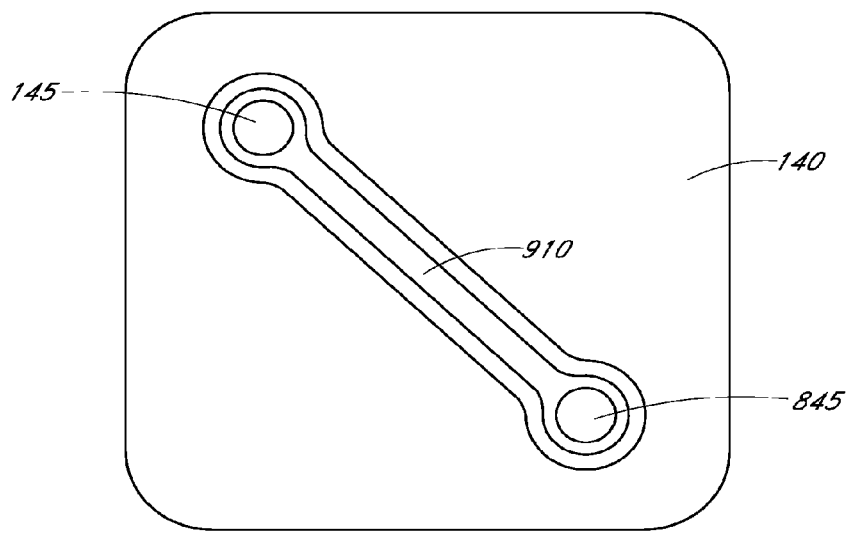
FIG. 9 illustrates a top view of a wound dressing including two orifices in a cover layer coupled through a fluid communication passage.

FIG. 9 illustrates a wound dressing in accordance with a further embodiment of the invention. The wound dressing of FIG. 9 is similar to that of FIGS. 1A-B but includes two orifices 145 and 845 provided in the cover layer 140. A fluid communication passage connects the two orifices such that a negative pressure applied to one of the orifices is communicated to the remaining orifice via the fluid communication passage. The orifices 145, 845 are located in opposite corner regions of the cover layer 140. The fluid communication passage is formed using a flexible molding 910 on the upper surface of the cover layer 140. It will be appreciated that the flexible molding may be formed from other suitable means for example a strip of transmission or open porous foam layer placed on the cover layer 140 between the orifices 145 and 845 and a further film welded or adhered over the strip thus sealing it to the cover layer and forming a passageway through the foam. A conduit may then be attached in a known manner to the sealing film for application of negative pressure.

In use, the wound dressing having two orifices is sealed over a wound site to form a wound cavity and an external source of negative pressure is applied to one of the orifices 145, 845, and the negative pressure will be communicated to the remaining orifice via the fluid communication passage. Thus, the negative pressure is communicated via the two orifices 145, 845 to the transmission layer 105, and thereby to the wound site. If one of the orifices 145, 845 becomes blocked due to wound exudate collecting at the orifice under the influence of gravity, the remaining orifice should remain clear, allowing negative pressure to continue to be communicated to the wound site. According to some embodiments, the transmission layer 105 may be omitted, and the two orifices will communicate the negative pressure to the wound site via the absorbent layer 110.

Figure 10:
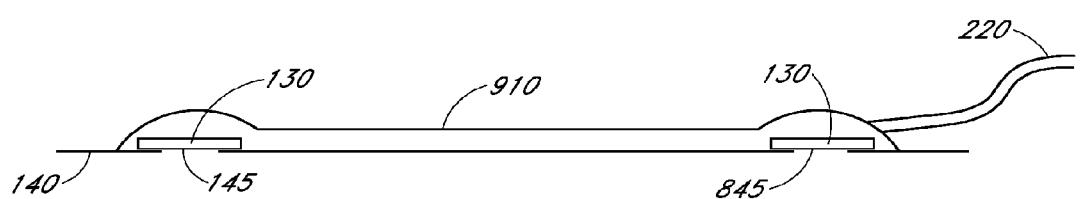
FIG. 10 illustrates an embodiment of the fluid communication passage.
Figure 11:
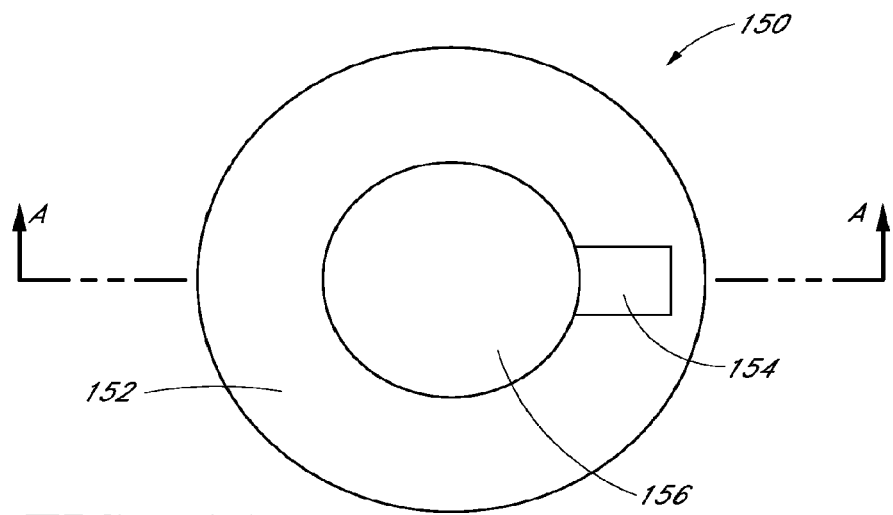
FIG. 11 illustrates a top view of a suction port.
Figure 12:
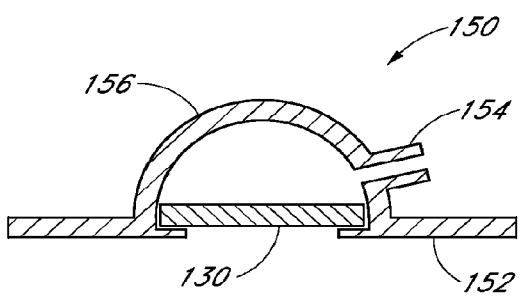
FIG. 12 illustrates a suction port including a filter element.
Figure 13:
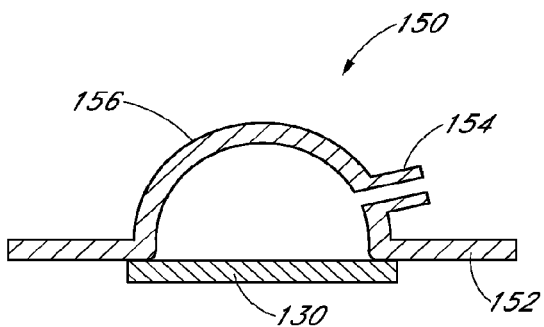
FIG. 13 illustrates a further suction port including a filter element.

FIG. 10 illustrates a side view of the fluid communication passage of the embodiment of FIG. 9. Molding 910 is sealed to the top surface of the cover layer 140, and covering orifices 145 and 845. Gas permeable liquid impermeable filter elements 130 are provided at each orifice. The molding 910 is coupled to an external source of negative pressure via a tube element 220.

According to some embodiments, a single filter element may be used extending underneath the length of the fluid communication passage and the two orifices. While the above example embodiment has been described as having two orifices, it will be understood that more than two orifices could be used, the fluid communication passage allowing the negative pressure to be communicated between the orifices.

Figure 16:
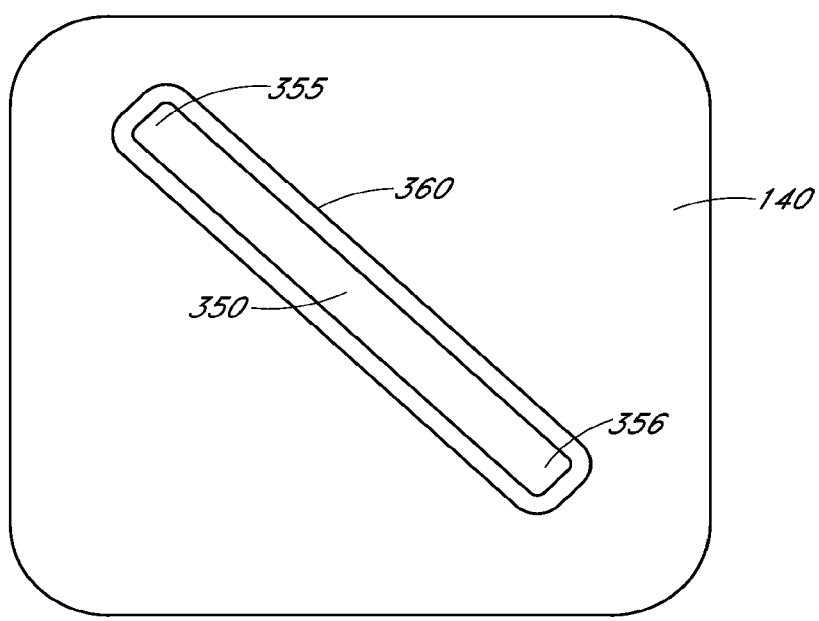
FIG. 16 illustrates a top view of a wound dressing including an elongate orifice in a cover layer.

FIG. 16 illustrates an alternative arrangement in which a single elongate orifice 350 is provided in the cover layer 140. First and second ends 355, 356 of the orifice 350 are located in opposite corner regions of the cover layer 140. A flexible molding 360 is sealed around the orifice 350 and allows negative pressure to be communicated through the cover layer 140 along the length of the orifice 350. The flexible molding 360 may be formed by any suitable means as described above in relation to flexible molding 910.

In use, the wound dressing is sealed over a wound site to form a wound cavity and an external source of negative pressure is applied to the orifice. If, due to the orientation of the wound dressing, wound exudate moves under the influence of gravity to collect around one end 355 of the orifice 350, a portion of the orifice 350 near to the end 355 will become blocked. However, a portion of the orifice near to the remaining end 356 should remain clear, allowing continued application of negative pressure to the wound site.

As still further options the dressing can contain antimicrobial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilized. As a still further option odor trapping elements such as activated carbon, cyclodextrine, zeolite or the like may be included in the absorbent layer or as a still further layer above the filter layer.

Figure 17:
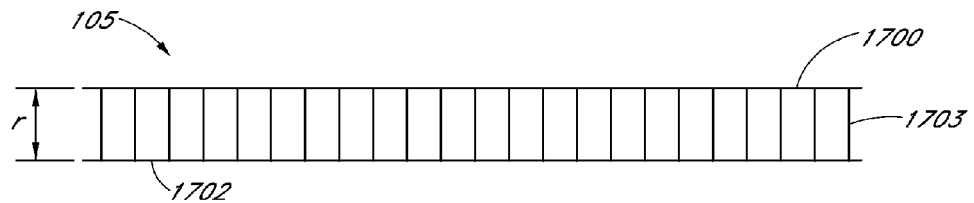
FIG. 17 illustrates a transmission layer in a relaxed mode of operation.

FIG. 17 illustrates a first, upper surface 1700 and a further, lower surface 1702 of a transmission layer 105 according to an embodiment of the present invention. In the embodiment illustrated in FIG. 17 fibers 1703 of a woven layer extend between the first surface 1700 and the further surface 1702. It will be appreciated that according to further embodiments of the present invention if a foam layer is used as a transmission layer 105 the connected strands forming the foam will act as spacer elements. As illustrated in FIG. 17 in a relaxed mode of operation, that is to say when in use, no negative pressure is applied to the wound dressing or negative pressure is applied to the wound dressing but no external force acts on the wound dressing then the fibers 1703 extend substantially perpendicular to the upper and lower surfaces keeping the surfaces in a spaced apart substantially parallel configuration.

Figure 18:
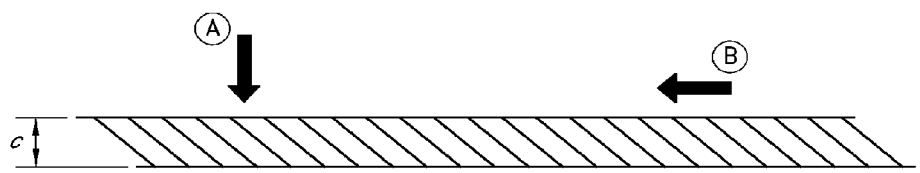
FIG. 18 illustrates a transmission layer in a forced mode of operation.

FIG. 18 illustrates the transmission layer 105 when an external force is exerted on the outside of the dressing. The external force can be a compressive force indicated by arrow A and/or a lateral force illustrated by arrow B in FIG. 18. As indicated either a compressive force or a lateral force acts to cause the fibers 1703 to lean to one side. This causes the upper and lower surfaces to become laterally offset with respect to each other as well as causing the thickness of the layer to reduce from a separation distance r indicated in FIG. 17 in a relaxed mode of operation to a compression distance c illustrated in FIG. 18. The reduction in thickness effectively provides some "give" in the dressing even when the dressing is subject to negative pressure. It will be appreciated that the forces acting on the dressing may occur throughout the whole of the surface area of the dressing or only in one or more particular regions. In such a situation regions of the dressing can be in a relaxed mode of operation and further regions can be in a compressed mode of operation. As illustrated in FIG. 18 when a force is exerted on the transmission layer the fibers separating the upper and lower surfaces tend to lean to one side sharing a common lean angle.

Throughout this specification reference will be made to a relaxed mode of operation and a forced mode of operation. It is to be understood that the relaxed mode of operation corresponds to a natural state of the material either when no negative pressure is applied or when negative pressure is applied. In either situation no external force, caused for example by motion of a patient or an impact is in evidence. By contrast a forced mode of operation occurs when an external force whether compressive, lateral or other is brought to bear upon the wound dressing. Such forces can cause serious damage/prevent healing or a wound.

Figure 19:
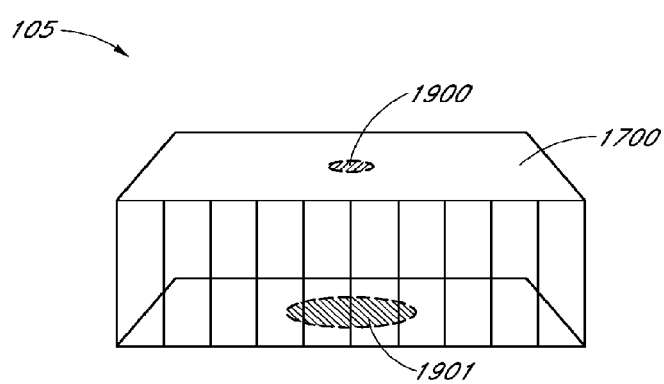
FIG. 19 illustrates pressure offsetting.

FIG. 19 illustrates how certain embodiments of the present invention can also operate to offset load forces. As illustrated in FIG. 19 if a force is exerted over a contact area 1900 in an upper surface 1700 of the transmission layer 105 then this force is transmitted across and through the transmission layer and is exerted over a larger dissipation area 1901 against an underlying wound site. In the case of use of a 3D knit as a transmission layer this is because the relatively stiff spacer elements provide at least some lateral stiffness to the layer.

Figure 20:
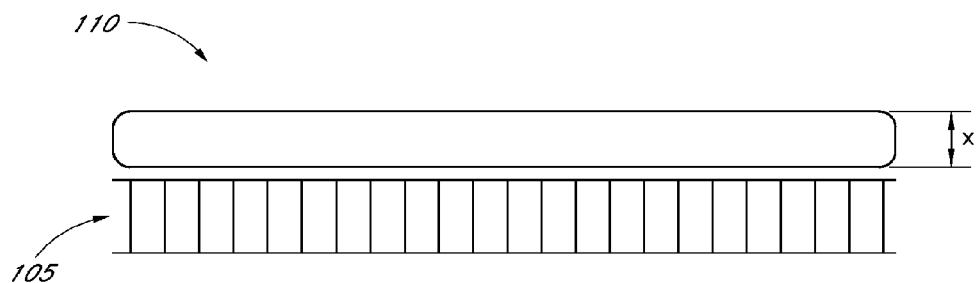
FIG. 20 illustrates a transmission layer and overlying absorbent layer in a relaxed mode of operation.
Figure 21:
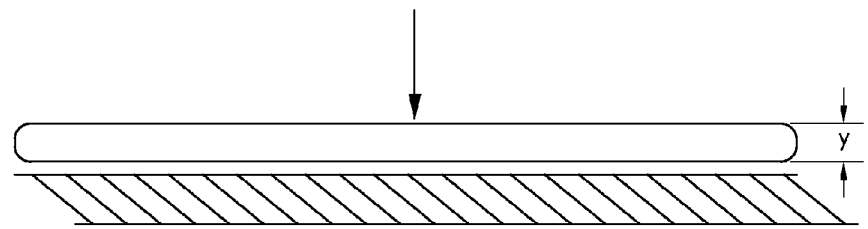
FIG. 21 illustrates an absorbent layer and transmission layer experiencing a compressive force.
Figure 22:
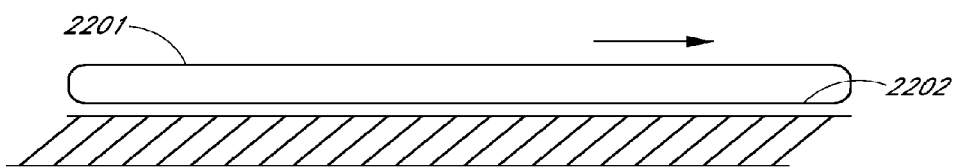
FIG. 22 illustrates an absorbent layer and transmission layer experiencing a shear force.

FIG. 20 illustrates the transmission layer 105 and absorbent layer 110 of some embodiments in more detail. The absorbent layer 110 is located proximate to the upper surface 1700 of the transmission layer 105 and is unbonded thereto according to certain embodiments of the present invention. When unbonded the absorbent layer 110 is also able to move laterally with respect to the underlying transmission layer when a lateral or shear force is applied to the wound dressing. Also the absorbent layer is able to further compress when a compressive force illustrated in FIG. 21 acts on the wound dressing. As illustrated in FIG. 21 the absorbent layer 110 decreases in thickness under a compressive force from a non-compressed thickness x illustrated in FIG. 20 to a compressed distance y illustrated in FIG. 21. The compressive force also acts to offset the upper and lower surfaces of the transmission layer as described above thus enhancing the "give" of the dressing. The ability for an upper surface 2201 to translate laterally with respect to a lower surface 2202 of the absorbent layer under a lateral or shearing force exerted on the wound dressing is illustrated in more detail in FIG. 22. This lateral motion causes the thickness x of the absorbent layer 110 to reduce and the upper surface and lower surface of the absorbent layer to be offset with respect to each other. This effect can itself be sufficient to prevent shear forces exerted on the whole or part of the wound dressing from being transferred to an underlying wound bed. As can the corresponding effect in the transmission layer. However a combination enhances the cushioning effect. If the wound bed comprises a skin graft region the reduction of shear forces can be particularly advantageous.

It is to be noted that in use the dressing may be used "up-side down", at an angle or vertical. References to upper and lower are thus used for explanation purposes only.

Figure 23:
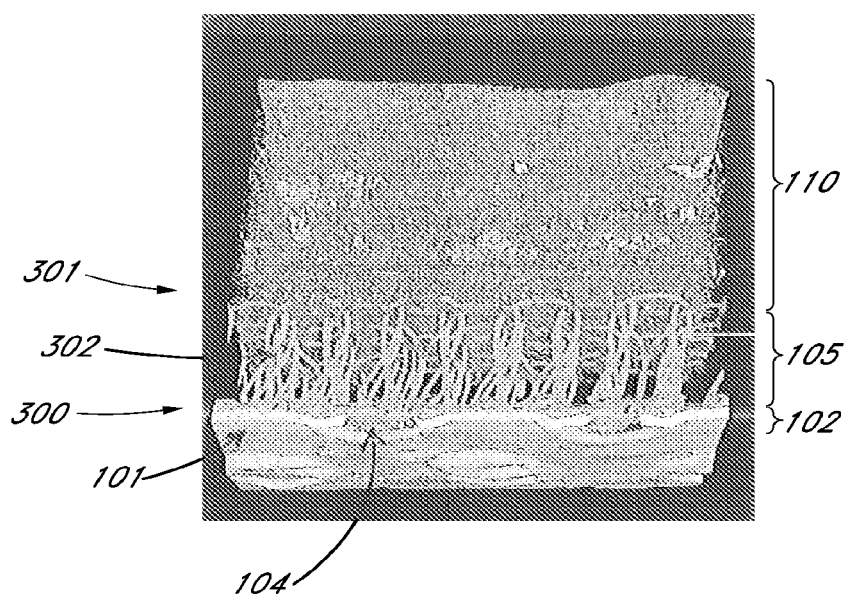
FIG. 23 illustrates a cross-section of a region of an embodiment of a wound dressing.

FIG. 23 illustrates a cross-section of a portion of an embodiment of a dressing shown in FIGS. 1A-2. In particular, FIG. 23 illustrates a magnified view of the wound contact layer 102 which includes a lower surface 101 and multiple perforations 104 formed as through holes. An upper surface 104 of the wound contact layer abuts a first layer 300 of the transmission layer 105. A further, upper, layer 301 of the transmission layer 105 is spaced apart from the first layer. The first and further layers of the transmission layer are kept apart in a spaced apart relationship by multiple mono-filament fiber spacers 302 which act as resilient flexible pillars separating the two layers of the transmission layer. The upper layer 301 of the transmission layer is adjacent a lower surface of the absorbent 110 which, for example, is formed as a pad of fibrous cellulose material interspaced with super-absorbent particulate matter.

Figure 24:
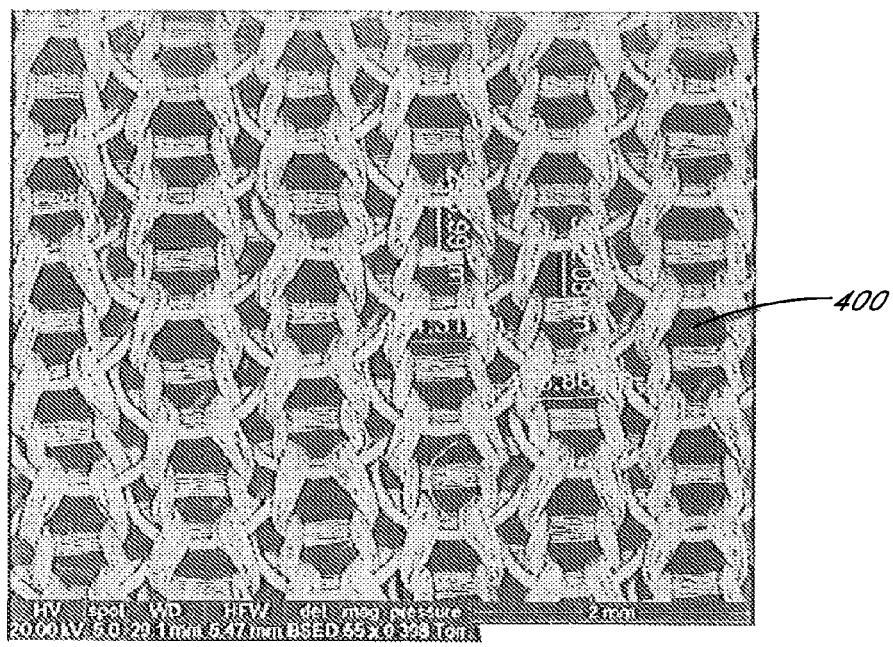
FIG. 24 illustrates a lower layer of a transmission layer used in an embodiment of a wound dressing.

FIG. 24 illustrates the lower layer of the 3D fabric transmission layer in more detail. The 3D fabric layer 105 is formed as a lower and upper knitted layer given a loft by the knitted structure. Rows of the knitted stitches may be referred to as a course of stitches. Columns of stitches may be referred to as a whale. A single monofilament fiber is knitted into the 3D fabric to form the multiple separating strands.

Figure 25:
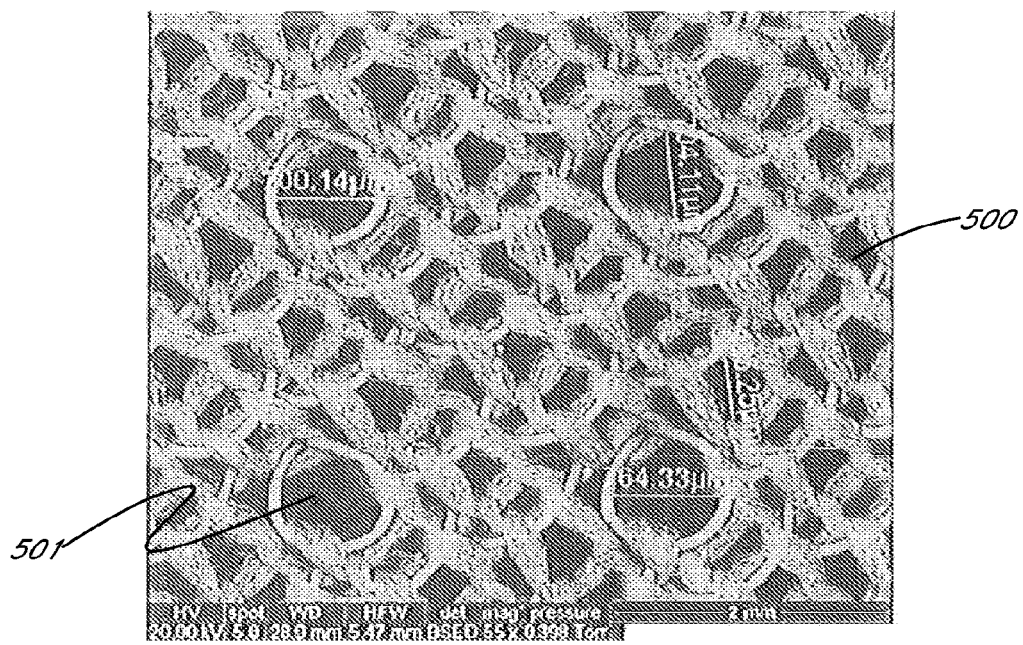
FIG. 25 illustrates an upper layer of a transmission layer used in an embodiment of a wound dressing.

As illustrated in FIG. 24 there are apertures or openings formed between interlocked stitches in the lower layer of the transmission layer 105. In use, wound exudate including liquid and semi-solid e.g. viscous slurry, suspensions of biological debris or the like and solid material will pass upwards through the perforations 104 in the wound contact layer and through the openings in the inter knitted structure of the first layer 300 of the transmission layer. The openings between the interconnected stitches have an average open area ranging from around 250 microns to 450 microns. The particular open area in the first layer of the transmission layer will be determined by the materials and method of manufacture of the lower layer. FIG. 25 illustrates how an open area of openings in the further layer above the first layer (that is to say further away from the wound) can include openings which have a greater open area than the openings in the lower layer. In this way as wound exudate which includes semi-solid and solid matter moves from the wound bed at the wound site upwards into the wound dressing any particulate matter which is of a size small enough to pass through the relative small openings 400 in the lower layer will certainly be able to pass through the larger area openings 501 in the upper area. This helps avoid debris in the form of solid material collecting in the interstitial region between the monofilament fibers between the upper and lower layer. As shown in FIG. 25, the upper layer 301 may include openings 500 similar to the openings 400 in the lower layer 300. However, during the knitting process the upper surface is knitted so that larger open area openings 501 are interspersed across the whole surface of the upper layer. As illustrated in FIG. 25 the larger open area openings 501 can have an open range considerably larger (shown between 700 to 800 microns). The lower layer 300 thus acts to some extent as a filtering layer having openings 400 which enable gas and liquid to pass freely therethrough but to prevent solid and semi-solid particulate matter which is too large from passing in to the interstitial region in the transmission layer 105. This helps keep a flowpath along the transmission layer open.

By providing openings in an upper layer in the transmission layer which have a greater open area than any openings in the lower area build-up of solid particulate matter in the interstitial region between the upper and lower layers of the transmission layer is avoided since any solid or semi-solid matter will flow along the channel and eventually be enabled to pass upwards through the larger openings where the material is taken up by the super-absorber/absorbent material.

The absorbent layer 110 holds liquid collected during the application of negative pressure therapy. By having this layer in fluid communication with, and preferably in contact with, the layer of the transmission layer, the region of the transmission layer 105 is kept at a moist environment. This helps avoid build-up and crusting of the exudate during use.

Figure 26:
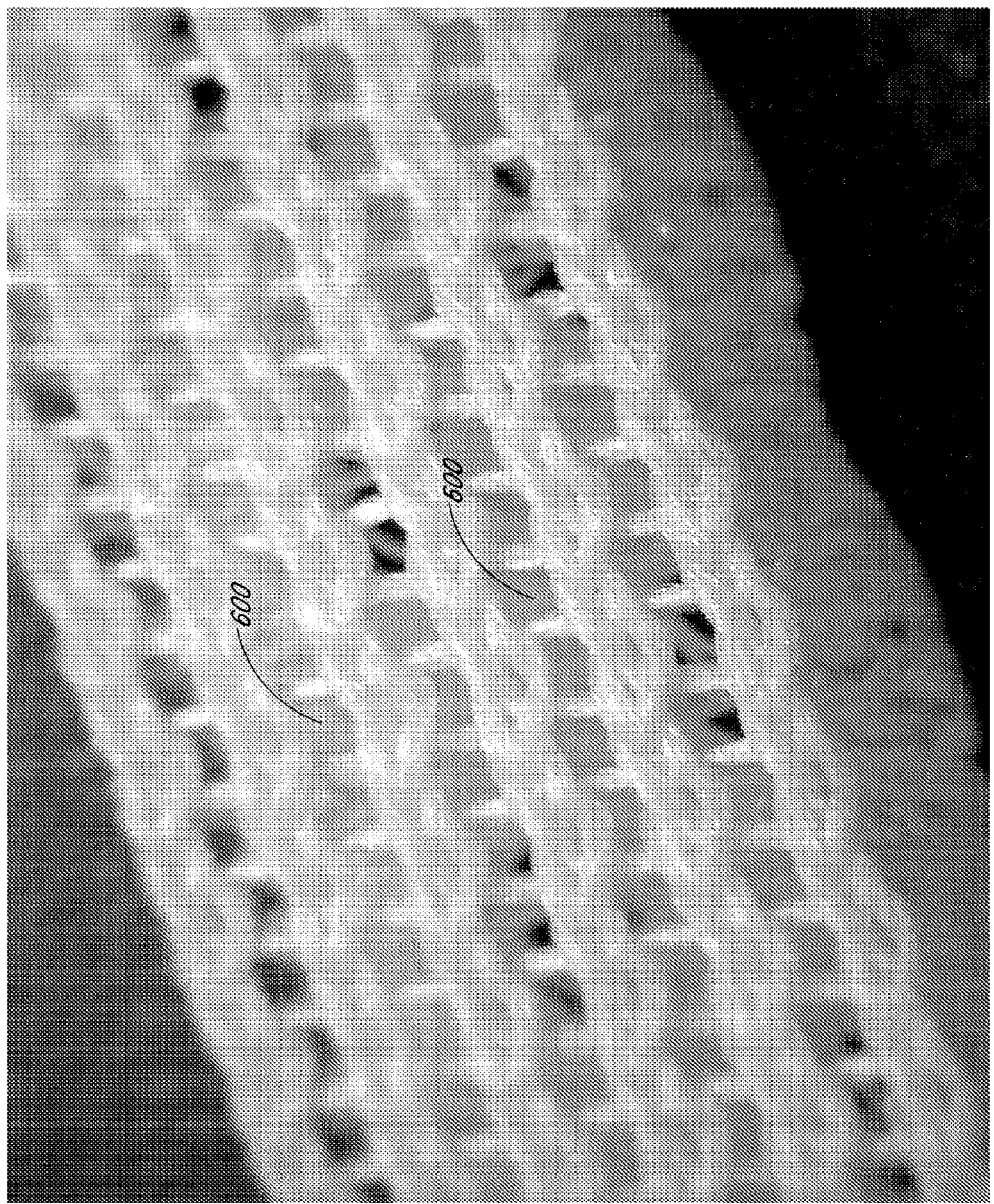
FIG. 26 illustrates a lower surface of a transmission layer used in another embodiment of a wound dressing.
Figure 27:
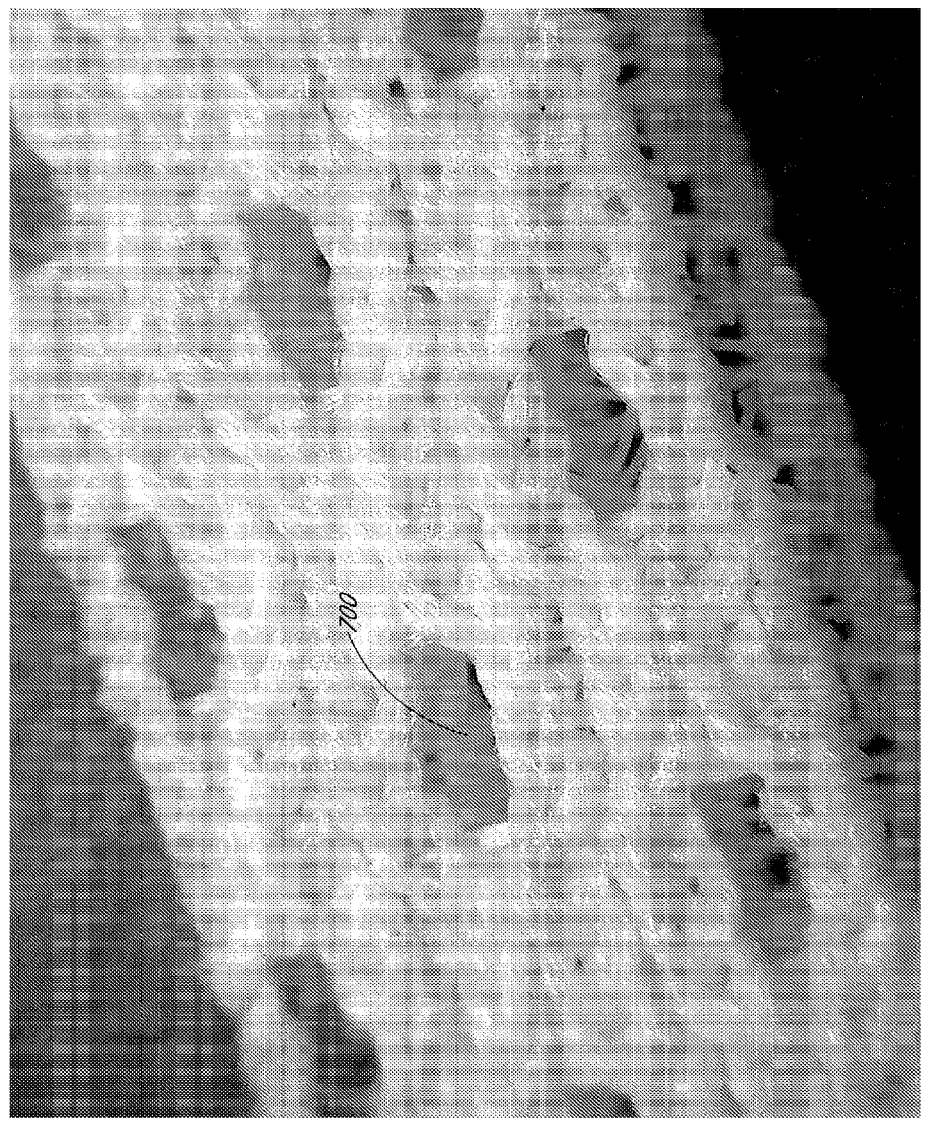
FIG. 27 illustrates an upper surface of a transmission layer used in another embodiment of a wound dressing.

FIG. 26 illustrates an alternative material which could be utilized as the transmission layer in a wound dressing. In particular, FIG. 26 illustrates a lower surface of a 3D knit material which may be utilized as the transmission layer. Openings 600 are formed in the surface which enables wound exudate and air to pass from the wound through a wound contact layer which would be located on the surface shown in FIG. 6 and through those openings. FIG. 27 illustrates an upper surface of the material shown in FIG. 26 and illustrates how larger openings 700 may be formed in the upper surface.

Whilst certain embodiments of the present invention have so far been described in which the transmission layer is formed as a 3D knit layer, e.g., two layers spaced apart by a monofilament layer, it will be appreciated that certain embodiments of the present invention are not restricted to the use of such a material. In some embodiments, as an alternative to such a 3D knit material one or more layers of a wide variety of materials could be utilized. In each case, according to embodiments of the present invention, the openings presented by layers of the transmission layer are wider and wider as one moves away from the side of the dressing which, in use will be located proximate to the wound. In some embodiments, the transmission layer may be provided by multiple layers of open celled foam. In some embodiments, the foam is reticulated open cell foam. Preferably, the foam is hydrophilic or able to wick aqueous based fluids. The pore size in each layer is selected so that in the foam layer most proximate to the wound side in use the pores have a smallest size. If only one further foam layer is utilized that includes pore sizes which are greater than the pore sizes of the first layer. This helps avoid solid particulate being trapped in the lower layer which thus helps maintain the lower layer in an open configuration in which it is thus able to transmit air throughout the dressing. In certain embodiments, two, three, four or more foam layers may be included. The foam layers may be integrally formed, for example, by selecting a foam having a large pore size and then repeatedly dipping this to a lesser and lesser extent into material which will clog the pores or alternatively, the transmission layer formed by the multiple foam layers may be provided by laminating different types of foam in a layered arrangement or by securing such layers of foam in place in a known manner.

According to certain embodiments of the present invention, the transmission layer is formed by multiple layers of mesh instead of foam or 3D knit materials. For example, fine gauze mesh may be utilized for a wound facing side of the transmission layer and a Hessian mesh having a larger pore size may be located on a distal side of the gauze mesh facing away from the wound in use. The one, two, three or more layers of mesh can be secured together in an appropriate manner, such as being stitched or adhered together or the like. The resultant mat of fibers provides a transmittal layer through which air can be transmitted in the dressing but by selecting the opening sizes in the meshes as one moves through the dressing away from the wound contact side, the accumulation of solid particulate matter in lower layers can be avoided.

Figure 28:
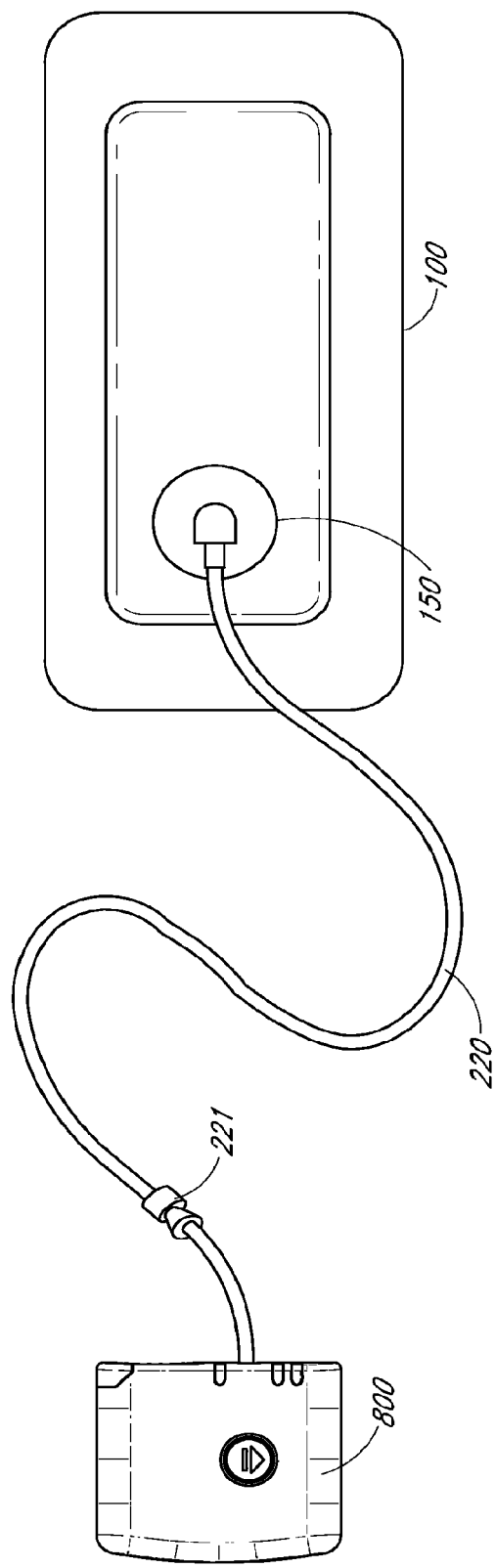
FIG. 28 illustrates an embodiment of a wound treatment system; and,
FIGS. 29A-D illustrate the use and application of an embodiment of a wound treatment system onto a patient.

FIG. 28 illustrates an embodiment of a TNP wound treatment comprising a wound dressing 100 in combination with a pump 800. Here, the dressing 100 may be placed over a wound as described previously, and a conduit 220 may then be connected to the port 150, although in some embodiments the dressing 100 may be provided with at least a portion of the conduit 220 preattached to the port 150. Preferably, the dressing 100 is provided as a single article with all wound dressing elements (including the port 150) pre-attached and integrated into a single unit. The wound dressing 100 may then be connected, via the conduit 220, to a source of negative pressure such as the pump 800. Preferably, the pump 800 is miniaturized and portable, although larger conventional pumps may also be used with the dressing 100. In some embodiments, the pump 800 may be attached or mounted onto or adjacent the dressing 100. A connector 221 may also be provided so as to permit the conduit 220 leading to the wound dressing 100 to be disconnected from the pump, which may be useful for example during dressing changes.

Figure 29A:
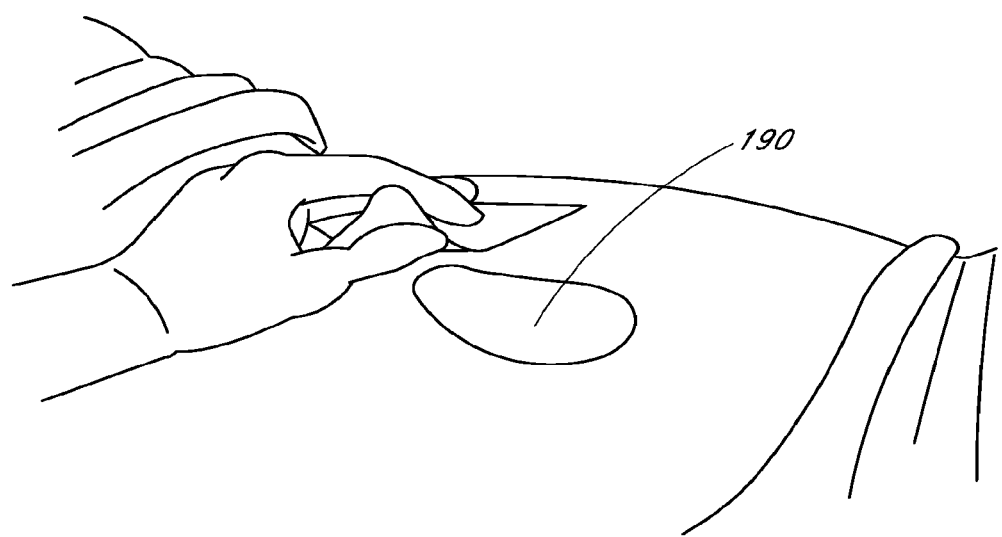

FIGS. 29A-D illustrate the use of an embodiment of a TNP wound treatment system being used to treat a wound site on a patient. FIG. 29A shows a wound site 190 being cleaned and prepared for treatment. Here, the healthy skin surrounding the wound site 190 is preferably cleaned and excess hair removed or shaved. The wound site 190 may also be irrigated with sterile saline solution if necessary. Optionally, a skin protectant may be applied to the skin surrounding the wound site 190. If necessary, a wound packing material, such as foam or gauze, may be placed in the wound site 190. This may be preferable if the wound site 190 is a deeper wound.

Figure 29B:
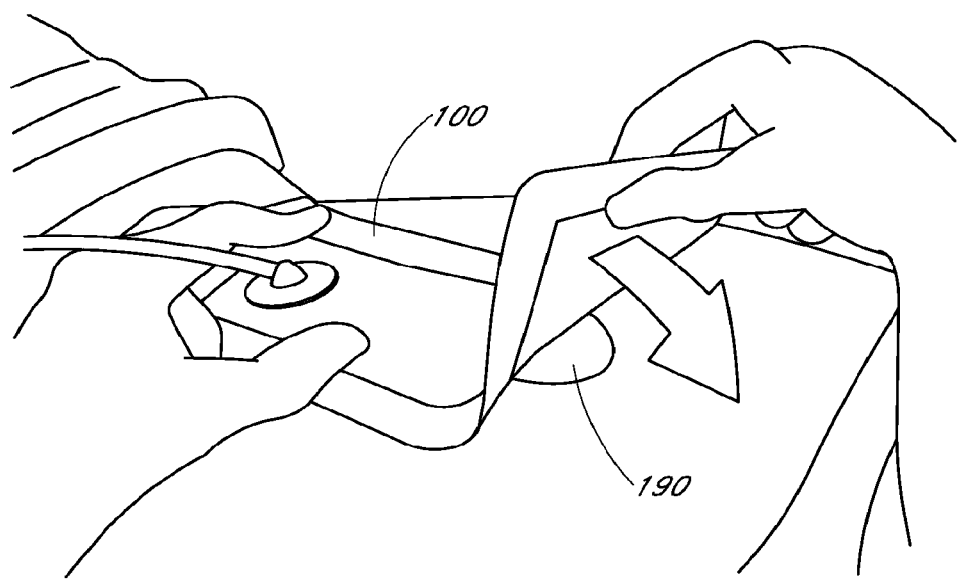

After the skin surrounding the wound site 190 is dry, and with reference now to FIG. 29B, the wound dressing 100 may be positioned and placed over the wound site 190. Preferably, the wound dressing 100 is placed with the wound contact layer 102 over and/or in contact with the wound site 190. In some embodiments, an adhesive layer is provided on the lower surface 101 of the wound contact layer 102, which may in some cases be protected by an optional release layer to be removed prior to placement of the wound dressing 100 over the wound site 190. Preferably, the dressing 100 is positioned such that the port 150 is in a raised position with respect to the remainder of the dressing 100 so as to avoid fluid pooling around the port. In some embodiments, the dressing 100 is positioned so that the port 150 is not directly overlying the wound, and is level with or at a higher point than the wound. To help ensure adequate sealing for TNP, the edges of the dressing 100 are preferably smoothed over to avoid creases or folds.

Figure 29C:
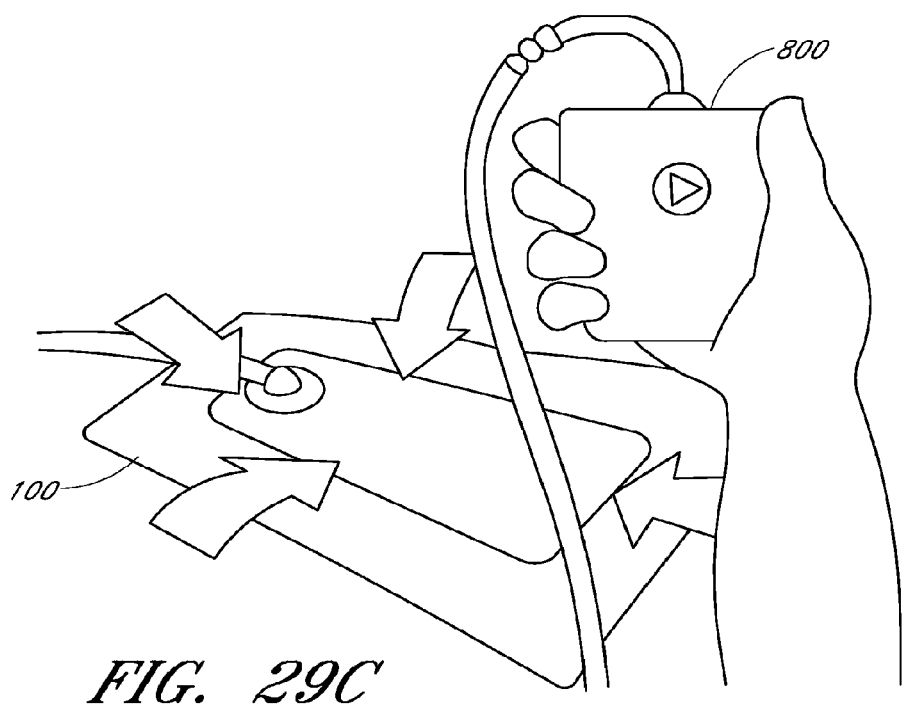

With reference now to FIG. 29C, the dressing 100 is connected to the pump 800. The pump 800 is configured to apply negative pressure to the wound site via the dressing 100, and typically through a conduit. In some embodiments, and as described above in FIG. 28, a connector may be used to join the conduit from the dressing 100 to the pump 800. Upon the application of negative pressure with the pump 800, the dressing 100 may in some embodiments partially collapse and present a wrinkled appearance as a result of the evacuation of some or all of the air underneath the dressing 100. In some embodiments, the pump 800 may be configured to detect if any leaks are present in the dressing 100, such as at the interface between the dressing 100 and the skin surrounding the wound site 190. Should a leak be found, such leak is preferably remedied prior to continuing treatment.

Figure 29D:
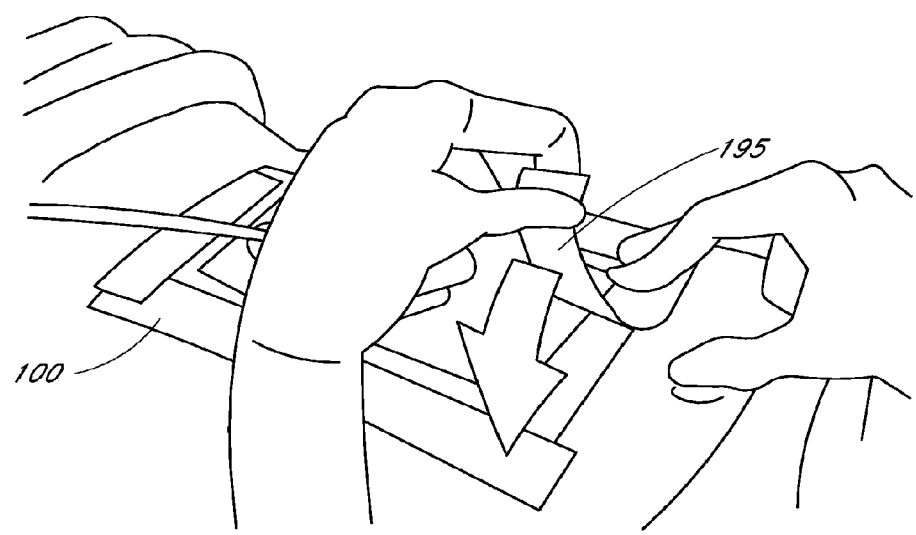

Turning to FIG. 29D, additional fixation strips 195 may also be attached around the edges of the dressing 100. Such fixation strips 195 may be advantageous in some situations so as to provide additional sealing against the skin of the patient surrounding the wound site 190. For example, the fixation strips 195 may provide additional sealing for when a patient is more mobile. In some cases, the fixation strips 195 may be used prior to activation of the pump 800, particularly if the dressing 100 is placed over a difficult to reach or contoured area.

Treatment of the wound site 190 preferably continues until the wound has reached a desired level of healing. In some embodiments, it may be desirable to replace the dressing 100 after a certain time period has elapsed, or if the dressing is full of wound fluids. During such changes, the pump 800 may be kept, with just the dressing 100 being changed.

Throughout the description and claims of this specification, the words "comprise" and "contain" and variations of the words, for example "comprising" and "comprises", mean "including but not limited to", and is they are not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. A wound treatment apparatus comprising:
    a wound dressing having a length extending between a first side and an opposing second side and a width extending between a third side and an opposing fourth side, the wound dressing comprising:
    an absorbent layer;
    at least one lower layer positioned beneath the absorbent layer, the at least one lower layer comprising an array of channels or vias each extending further along the length of the wound dressing than along the width of the wound dressing, each of the channels or vias defining an elongate shape, each elongate shape extending through an entire depth of the at least one lower layer; and
    a cover layer overlying the absorbent layer and comprising an orifice configured to communicate negative pressure from a source of negative pressure to a wound site through at least the absorbent layer and the at least one lower layer.

2. The apparatus of claim 1, wherein the plurality of channels or vias comprises a staggered array of channels or vias.

3. The apparatus of claim 2, wherein the channels or vias do not intersect with each other.

4. The apparatus of claim 1, wherein the channels or vias abut the absorbent layer.

5. The apparatus of claim 1, wherein the absorbent layer comprises superabsorbent material.

6. The apparatus of claim 1, wherein the absorbent layer comprises a gel forming material.

7. The apparatus of claim 1, wherein the absorbent layer comprises at least one through hole.

8. The apparatus of claim 7, wherein the absorbent layer comprises multiple openings extending through a thickness of the absorbent layer.

9. The apparatus of claim 1, wherein the wound dressing further comprises a wound contact layer below the at least one lower layer.

10. The apparatus of claim 1, wherein the wound dressing further comprises a suction port provided over the orifice for applying negative pressure from the source of negative pressure to the wound site through at least the absorbent layer and the at least one lower layer.

11. The apparatus of claim 10, wherein the wound dressing further comprises a filter element sealed to the suction port and/or cover layer over the orifice.

12. The apparatus of claim 1, further comprising a negative pressure source configured to communicate negative pressure to the wound site through the orifice.

13. A wound treatment apparatus comprising:
a wound dressing having a length extending between a first side and an opposing second side and a width extending between a third side and an opposing fourth side, the wound dressing comprising:
a cover layer comprising an orifice;
a foam layer positioned beneath the cover layer; and
at least one lower layer positioned beneath the foam layer, the at least one lower layer comprising an array of channels or vias each extending further along the length of the wound dressing than along the width of the wound dressing, each of the channels or vias defining an elongate shape, each elongate shape extending through an entire depth of the at least one lower layer;
wherein the orifice in the cover layer is configured to communicate negative pressure from a source of negative pressure to a wound site through at least the foam layer and the at least one lower layer.

14. The apparatus of claim 13, wherein the foam layer extends outward beyond an edge region of the at least one lower layer.

15. The apparatus of claim 13, wherein the plurality of channels or vias comprises a staggered array of channels or vias.

16. The apparatus of claim 15, wherein the channels or vias do not intersect with each other.

17. The apparatus of claim 13, wherein the wound dressing further comprises a wound contact layer below the at least one lower layer.

18. The apparatus of claim 13, wherein the wound dressing further comprises a suction port provided over the orifice for applying negative pressure from the source of negative pressure to the wound site through at least the foam layer and the at least one lower layer.

19. The apparatus of claim 18, wherein the wound dressing further comprises a filter element sealed to the suction port and/or cover layer over the orifice.

20. The apparatus of claim 13, further comprising a negative pressure source configured to communicate negative pressure to the wound site through the orifice.

21. A wound treatment apparatus comprising:
a wound dressing comprising:
a flexible, perforated wound contact layer;
a transmission layer positioned above the wound contact layer;
an absorbent layer positioned above the transmission layer; and
a cover layer comprising an orifice, the cover layer overlying the wound contact layer, the transmission layer and the absorbent layer;
wherein the orifice in the cover layer is configured to communicate negative pressure from a source of negative pressure to a wound site through at least the absorbent layer, the transmission layer and the wound contact layer; and
wherein the absorbent layer comprises a through hole situated underneath the orifice.

22. The apparatus of claim 21, wherein the cover layer is sealed to the wound contact layer.

23. The apparatus of claim 21, wherein the absorbent layer comprises superabsorbent material.

24. The apparatus of claim 21, wherein the absorbent layer comprises a gel forming material.

25. The apparatus of claim 21, wherein the absorbent layer is in contact with the cover layer.

26. The apparatus of claim 21, wherein the wound dressing further comprises a suction port provided over the orifice for applying negative pressure from the source of negative pressure to the wound site through at least the absorbent layer, the transmission layer and the wound contact layer, wherein the through hole in the absorbent layer is situated underneath the suction port.

27. The apparatus of claim 26, further comprising a filter element sealed to the suction port and/or cover layer over the orifice.

28. The apparatus of claim 21, further comprising a negative pressure source configured to communicate negative pressure to the wound site through the orifice.

29. The apparatus of claim 1, wherein each elongate shape extends linearly through an entire depth of the at least one lower layer.

30. The apparatus of claim 13, wherein each elongate shape extends linearly through an entire depth of the at least one lower layer.

* * * * *

UNITED STATES PATENT AND TRADEMARK OFFICE
CERTIFICATE OF CORRECTION

PATENT NO. : 10,159,604 B2
APPLICATION NO. : 15/633670
DATED : December 25, 2018
INVENTOR(S) : Gordon Campbell Adie Page 1 of 1

It is certified that error appears in the above-identified patent and that said Letters Patent is hereby corrected as shown below:

On the Title Page

Page 8, Column 2, item (56), OTHER PUBLICATIONS, Line 2, delete "Plas" and insert --Plast--.

Page 9, in Column 2, item (56), OTHER PUBLICATIONS, Line 42, delete "Orthopadic" and insert --Orthopaedic--.

In the Specification

Column 10, Line 46, delete "layers," and insert --layers),--.

Column 11, Line 15, delete "Chem-PositeTM11C-450." and insert --Chem-PositeTM 11C-450.--.

Signed and Sealed this
Eighteenth Day of February, 2020

Andrei Iancu
*Director of the United States Patent and Trademark Office*